US008052659B2

(12) United States Patent
Ravenscroft et al.

(10) Patent No.: US 8,052,659 B2
(45) Date of Patent: Nov. 8, 2011

(54) CATHETER DEVICE

(75) Inventors: Adrian Ravenscroft, Rochester, MA (US); Yimin Yang, Medfield, MA (US); Michael Igoe, Perkasie, PA (US)

(73) Assignee: Phase One Medical LLC, Hingham, MA (US)

( * ) Notice: Subject to any disclaimer, the term of this patent is extended or adjusted under 35 U.S.C. 154(b) by 599 days.

(21) Appl. No.: 11/559,092

(22) Filed: Nov. 13, 2006

(65) Prior Publication Data
US 2007/0232981 A1 Oct. 4, 2007

Related U.S. Application Data

(60) Provisional application No. 60/735,257, filed on Nov. 10, 2005.

(51) Int. Cl.
*A61M 25/00* (2006.01)
*A61B 10/00* (2006.01)
(52) U.S. Cl. ......... 604/264; 600/564; 600/567; 604/247
(58) Field of Classification Search .................. 600/435; 604/247, 264; 606/159
See application file for complete search history.

(56) References Cited

U.S. PATENT DOCUMENTS

| | | | |
|---|---|---|---|
| 4,137,906 A | 2/1979 | Akiyama et al. | |
| 4,180,068 A | 12/1979 | Jacobsen et al. | |
| 4,509,946 A | 4/1985 | McFarlane | |
| 4,643,712 A | 2/1987 | Kulik et al. | |
| 4,693,257 A | 9/1987 | Markham | |
| 4,727,873 A | 3/1988 | Mobin-Uddin | |
| 5,030,210 A | 7/1991 | Alchas | |
| 5,100,424 A | 3/1992 | Jang et al. | |
| 5,112,301 A | 5/1992 | Fenton et al. | |
| 5,209,723 A | 5/1993 | Twardowski et al. | |
| 5,224,938 A | 7/1993 | Fenton, Jr. | |
| 5,250,034 A | 10/1993 | Appling et al. | |
| 5,261,885 A | 11/1993 | Lui | |

(Continued)

FOREIGN PATENT DOCUMENTS

EP  1374941 A1  1/2004

(Continued)

OTHER PUBLICATIONS

Int'l Search Report for PCT/US06/43961 [WO2007/059018] which claims priority to U.S. Appl. No. 60/735,257, filed Nov. 10, 2005.

(Continued)

*Primary Examiner* — Nicholas D Lucchesi
*Assistant Examiner* — Ian K Holloway
(74) *Attorney, Agent, or Firm* — Shay Glenn LLP

(57) ABSTRACT

A catheter device has an elongate body and a chamber positioned within the elongate body. The chamber has a chamber opening, and a barrier, such as a gate, moves over the chamber opening. The barrier moves between an uncovered position uncovering the chamber opening and a covered position covering the chamber opening. The catheter has at least one cutting edge by the chamber opening. In particular, the at least one cutting edge may be on the barrier, where the at least one cutting edge is guided over the chamber opening with movement of the barrier between the uncovered position and the covered position. The cutting edge cuts away a fibrin sheath blocking the chamber opening. The catheter may have multiple chambers connected by channels that allow the chambers to be flushed to prevent microbial colonization.

31 Claims, 21 Drawing Sheets

U.S. PATENT DOCUMENTS

| | | | |
|---|---|---|---|
| 5,304,155 A | 4/1994 | Lui | |
| 5,324,304 A | 6/1994 | Rasmussen | |
| 5,360,403 A | 11/1994 | Mische | |
| 5,405,320 A | 4/1995 | Twardowski et al. | |
| 5,421,832 A | 6/1995 | Lefebvre | |
| 5,484,384 A | 1/1996 | Fearnot | |
| 5,509,897 A | 4/1996 | Twardowski et al. | |
| 5,542,933 A | 8/1996 | Marks | |
| 5,569,182 A | 10/1996 | Twardowski et al. | |
| 5,578,010 A | 11/1996 | Ashby | |
| 5,685,867 A | 11/1997 | Twardowski et al. | |
| 5,730,717 A | 3/1998 | Gelbfish | |
| 5,792,118 A | 8/1998 | Kurth et al. | |
| 5,807,329 A | 9/1998 | Gelman | |
| 5,807,349 A | 9/1998 | Person et al. | |
| 5,807,356 A | 9/1998 | Finch, Jr. et al. | |
| 5,857,464 A | 1/1999 | Desai | |
| 5,891,091 A | 4/1999 | Teirstein | |
| 5,938,582 A | 8/1999 | Ciamacco, Jr. et al. | |
| 5,961,486 A | 10/1999 | Twardowski et al. | |
| 5,968,071 A | 10/1999 | Chevillon et al. | |
| 5,989,213 A | 11/1999 | Maginot | |
| 6,007,558 A | 12/1999 | Ravenscroft et al. | |
| 6,027,514 A * | 2/2000 | Stine et al. | 606/159 |
| 6,052,612 A | 4/2000 | Desai | |
| 6,074,339 A | 6/2000 | Gambale et al. | |
| 6,074,374 A | 6/2000 | Fulton | |
| 6,099,518 A | 8/2000 | Adams et al. | |
| 6,102,891 A | 8/2000 | Maria van Erp | |
| 6,149,607 A * | 11/2000 | Simpson et al. | 600/567 |
| 6,183,438 B1 | 2/2001 | Berguer | |
| 6,213,976 B1 | 4/2001 | Trerotola | |
| 6,258,026 B1 | 7/2001 | Ravenscroft et al. | |
| 6,267,775 B1 | 7/2001 | Clerc et al. | |
| 6,325,778 B1 | 12/2001 | Zadno-Azizi et al. | |
| 6,352,521 B1 | 3/2002 | Prosl | |
| 6,355,014 B1 | 3/2002 | Zadno-Azizi et al. | |
| 6,361,545 B1 | 3/2002 | Macoviak et al. | |
| 6,364,867 B2 | 4/2002 | Wise et al. | |
| 6,375,654 B1 | 4/2002 | McIntyre | |
| 6,514,191 B1 | 2/2003 | Popowski et al. | |
| 6,579,302 B2 | 6/2003 | Duerig et al. | |
| 6,592,544 B1 * | 7/2003 | Mooney et al. | 604/43 |
| 6,638,233 B2 * | 10/2003 | Corvi et al. | 600/564 |
| 6,645,160 B1 * | 11/2003 | Heesch | 600/585 |
| 6,701,180 B1 | 3/2004 | Desai | |
| 6,872,217 B2 | 3/2005 | Walak et al. | |
| 6,881,218 B2 | 4/2005 | Beyer et al. | |
| 6,923,822 B2 | 8/2005 | Crawford et al. | |
| 6,932,829 B2 | 8/2005 | Majercak | |
| 6,936,058 B2 | 8/2005 | Forde et al. | |
| 7,282,041 B2 | 10/2007 | Igarashi et al. | |
| 2002/0026156 A1 | 2/2002 | Quinn | |
| 2003/0144623 A1 | 7/2003 | Heath et al. | |
| 2003/0212431 A1 | 11/2003 | Brady et al. | |
| 2004/0030319 A1 | 2/2004 | Korkor et al. | |
| 2004/0034329 A1 | 2/2004 | Mankus et al. | |
| 2004/0082909 A1 | 4/2004 | Shia et al. | |
| 2004/0092890 A1 | 5/2004 | Ash | |
| 2004/0181191 A1 | 9/2004 | Teitelbaum | |
| 2004/0210180 A1 | 10/2004 | Altman | |
| 2004/0210187 A1 | 10/2004 | Zawacki | |
| 2005/0038413 A1 | 2/2005 | Sansoucy | |
| 2005/0165419 A1 * | 7/2005 | Sauer et al. | 606/148 |
| 2005/0228339 A1 | 10/2005 | Clark | |
| 2005/0245900 A1 | 11/2005 | Ash | |
| 2005/0256461 A1 | 11/2005 | DiFiore et al. | |
| 2005/0288704 A1 | 12/2005 | Cartier et al. | |
| 2006/0079928 A1 | 4/2006 | Cartier et al. | |
| 2006/0253063 A1 | 11/2006 | Schweikert | |
| 2007/0198050 A1 | 8/2007 | Ravenscroft et al. | |
| 2007/0225661 A1 | 9/2007 | Ash et al. | |
| 2007/0225682 A1 | 9/2007 | Ash et al. | |
| 2008/0287888 A1 | 11/2008 | Ravenscroft et al. | |

FOREIGN PATENT DOCUMENTS

| | | |
|---|---|---|
| JP | 2001-137350 A | 5/2001 |
| WO | 01/15609 A1 | 3/2001 |
| WO | WO 01/15609 * | 3/2001 |
| WO | WO 02/28286 A1 | 4/2002 |
| WO | WO 2007/059018 A2 | 5/2007 |

OTHER PUBLICATIONS

Franco et al.; Effective central venous catheter hemodialysis with a novel needlefree connection device (TEGO}); Aug. 2004.

G2 Filter System (Information for Use); G2 Filter System Jugular/Subclavian Vein Approach; Bard Peripheral Vascular, Inc.; 2005.

G2 Filter System (Information for Use); G2 Filter System Femoral Vein Approach; Bard Peripheral Vascular, Inc.; 2005.

Recovery Cone® Removal System for use with the Recovery® Filter (Information for Use); Bard Peripheral Vascular, Inc.; 2005.

* cited by examiner

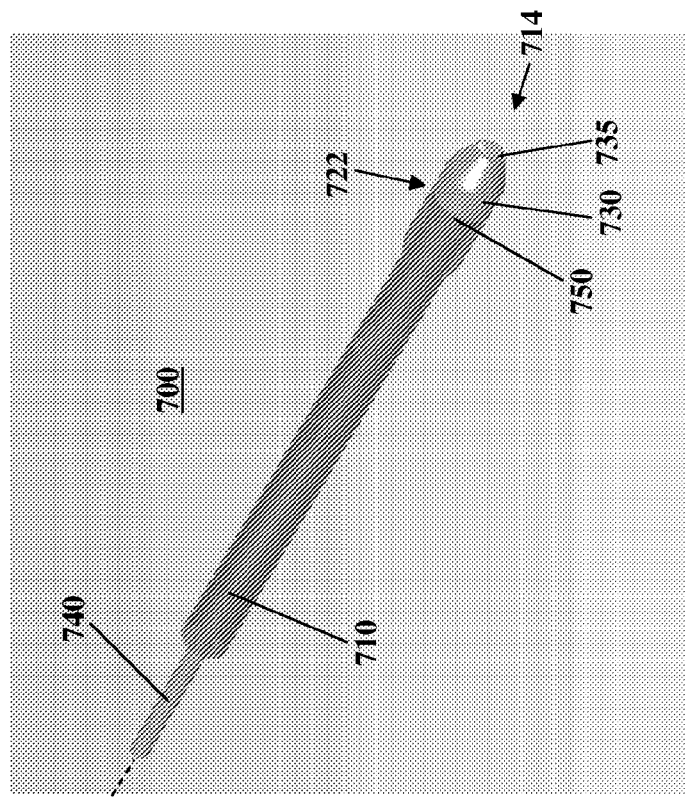
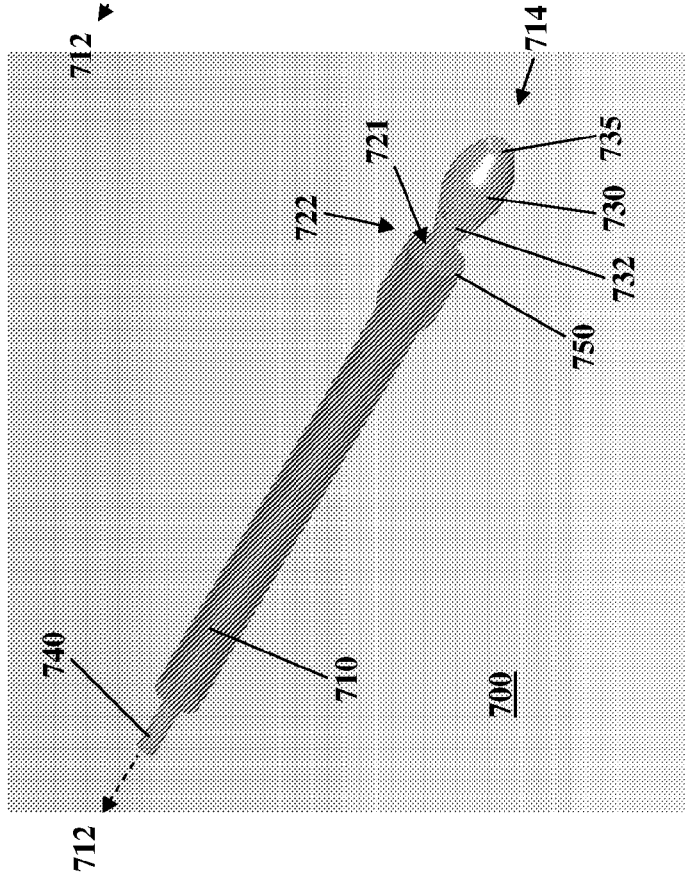
FIGURE 7A
FIGURE 7B

CATHETER DEVICE

CROSS REFERENCE TO RELATED APPLICATIONS

This application claims priority to U.S. Provisional Application No. 60/735,257 filed Nov. 10, 2005, the contents of which are incorporated herein by reference.

BACKGROUND OF THE INVENTION

1. Field of the Invention

This invention relates generally to catheters, and more particularly, to a venous catheter adapted to prevent catheter failure caused by thrombus or fibrin formation at the distal end of the catheter and to prevent microbial infection.

2. Description of Related Art

The use of cuffed tunneled central venous catheters has become widely accepted as a viable option for prolonged temporary vascular access as well as permanent vascular access for hemodialysis. It is estimated that 7 million central venous catheters (CVCs) will be inserted into patients annually in the United States. Unfortunately, the durability of central venous catheters is limited by catheter malfunction, primarily manifested by insufficient flow or total catheter lumina occlusion.

A variety of catheter designs exist on the market. Some catheter designs are simple in nature and have a single lumen that extends through an elongate body, while other designs employ two or three lumens. Each lumen has an opening at, or near, the distal tip of the catheter body. More recently, the focus of catheter design has focused on tip geometries that are supposed to provide lower occlusion rates and higher flow rates. Despite the various existing catheter designs, the primary patency rate has been reported to be a dismal 65% at 1 year and in some institutions as low as 45% at 1 year.

To help prevent occlusion, the current clinical practice is to "lock" catheters with Heparin (5000 U/mL) This practice attempts to create a highly anticoagulant environment within each catheter lumen. This practice has inherent risks of systemic anticoagulation since most catheters can hold at least 3 mL of Heparin resulting in a dosing potential of 15,000 U. Furthermore, despite the high concentration of anticoagulant, central venous catheters are still prone to partial or total occlusion leading to poor or failed dialysis.

Failure of hemodialysis catheter patency often results from the accumulation of obstructing thrombus or fibrin at the distal tip of the catheter. Fibrin accumulation may cause failure of smaller single-, double- and triple lumen central venous catheters, but the problem is more significant with hemodialysis catheters, because even partial encroachment of fibrin on the catheter lumen can prevent the high flow rates required for satisfactory hemodialysis. Instillation of Urokinase or tPA into each catheter lumen for thirty minutes in the hemodialysis unit may restore patency to the catheter by lysing thrombosis at the catheter tip, but the effect is often transient or ineffective. No current consensus exists as to what further method is optimal for maintaining catheter patency in patients with regard to catheter failure caused by fibrin sheath formation.

It is also believed that poor catheter position or catheter kinking may also be partially responsible for the low patency rates.

A serious complication that may arise with the use of catheters is infection caused by microbial colonization on the catheter. Even using the best available aseptic techniques during insertion and maintenance of the catheter, one out of every twenty CVCs inserted will be associated with at least one episode of blood stream infection. As a result, it is estimated that more than 300,000 episodes of CVC-related bloodstream infections (CRBSI) will occur annually in the United States. On average, each episode of CRBSI will cost almost $30,000 per survivor and result in an additional average stay of 6.5 days in the ICU.

For long-term catheters, the hub is believed to be a major source of microbial colonization for the catheter lumen, ultimately leading to bloodstream infections through luminal colonization of the intravascular segment.

The surfaces of indwelling medical devices act as a suitable substratum for microbial colonization leading to life threatening infections. Organisms that adhere to the catheter surface maintain themselves by producing a substance rich in exopolysaccharides, often referred to as a fibrous microbial biofilm. The organisms, i.e. bacteria, embed themselves in the biofilm layer, becoming more resistant to the antimicrobial activity of glycopeptide antibiotics. Following catheter insertion, a thrombin sheath rich in host proteins covers the internal and external surface of the catheter. The proteins in the thrombin sheath—such as fibrin, fibrinogen, fibronectin, laminin, thrombospondin, and collagen—act as adhesions. Organisms, such as staphylococci, bind to fibronectin. *Staphylococcuss aureus* binds strongly to both fibronectin and fibrinogen, while *Candida albicans* binds well to fibrin. This process observed at the molecular level, is translated into a correlation at the clinical level between thrombogenesis and infection.

In one study, it was determined that catheter related bacteraemia (CRB) is the most significant complication of hemodialysis catheters occurring in 5-18% of catheters or in 3.9-8.6 episodes/1000 catheter days. It is also reported that the cumulative hazard of developing CRB revealed a roughly linear increase in cumulative hazard, suggesting that the risk of developing CRB is constant over time (catheterization days). This suggests that infection is random, there is no threshold effect, and the chance of infection is not related to how long the catheter has been implanted.

Accordingly, it is evident that central venous catheters are plagued with a variety of complications and no existing design has successfully addressed all clinical issues. The most prevalent mechanical complication is occlusion of the distal tip followed by catheter fracture. Although catheter occlusion is not as serious as CRB since it rarely causes death, it does lead to additional non-elective therapies such as tPA instillation and catheter exchange (~10%). It is evident that the current catheter designs do not provide a reliable means to prevent distal tip thrombosis. In addition, distal tip fouling caused by catheter misplacement, transmural tip incorporation, and external fibrin sheath formation negatively influences catheter performance. Furthermore, microbial colonization on the catheter presents the risk of life-threatening infection.

SUMMARY OF THE INVENTION

In view of the problems described previously, the present invention provides a catheter design that attempts to address the complications associated with central venous catheters. It is an object of the present invention to provide a catheter structure designed to minimize fibrin sheath development and distal tip thrombosis at, or near, the distal tip of the catheter, which inhibit flow into or out of the catheter lumen or lumens. It is a further object of the present invention to provide a catheter that minimizes the risk of microbial infection.

Accordingly, an embodiment of the present invention provides a catheter device with an elongate body and a chamber positioned within the elongate body. The chamber has a chamber opening, and a barrier moves over the chamber opening. The barrier moves between an uncovered position uncovering the chamber opening and a covered position covering the chamber opening. The catheter has at least one cutting edge positioned by the chamber opening. In particular, the at least one cutting edge may be positioned on the barrier, where the at least one cutting edge is guided over the chamber opening with movement of the barrier between the uncovered position and the covered position. In addition, the barrier may be a gate positioned within the chamber. Moreover, to ensure proper positioning of the catheter, the catheter may employ a centering mechanism for spacing the catheter device from walls of the body passageway in which the catheter is deployed.

The present invention also provides a method for operating the catheter described above to remove fibrin sheath development at, or near, the distal tip of the catheter. The method involves moving the barrier to the uncovered position, applying a vacuum in the chamber to draw fibrin near the opening into the chamber, and cutting fibrin near the chamber opening by moving the barrier from the uncovered position to the covered position.

Another embodiment of the present invention provides a catheter device with an elongate body and a chamber positioned within the elongate body. The chamber has a chamber opening and a barrier moves over the chamber opening. A control wire is connected to the barrier and controls movement of the barrier. The control wire may be positioned in a control wire channel extending along the elongate body. In addition, the control wire may be controlled by a control mechanism, such as a button on a hub, positioned at a proximal end of the elongate catheter body.

Yet another embodiment of the present invention provides a catheter device with an elongate body with a first chamber and a second chamber positioned within the elongate body. The first chamber has a first chamber opening and the second chamber has a second chamber opening. A first barrier moves over the first chamber opening. A first cutting edge is positioned by the first chamber opening. In particular, the first cutting edge may be positioned on the first barrier and guided over the first chamber opening with movement of the first barrier over the first chamber opening. A second barrier moves over the second chamber opening. In particular, the second cutting edge may be positioned on the second barrier and guided over the second chamber opening with movement of the second barrier over the second chamber opening. The catheter may have an interior dividing wall positioned between the first chamber and the second chamber. In addition, the catheter may have at least one connecting channel positioned in the interior dividing wall and extending between the first chamber and the second chamber. Accordingly, the present invention provides a method of flushing the catheter to prevent infection caused by microbial colonization on the catheter. The method involves moving the first barrier over the first chamber opening, moving the second barrier over the second chamber opening, and introducing fluid into the first chamber to cause fluid circulation through the first chamber, the at least one connecting channel, and the second chamber.

These and other aspects of the present invention will become more apparent from the following detailed description of the preferred embodiments of the present invention when viewed in conjunction with the accompanying drawings.

BRIEF DESCRIPTION OF THE DRAWINGS

FIG. 7A illustrates the distal end of an exemplary embodiment with a single interior chamber and a valve plug in an open valve position.

FIG. 7B illustrates the distal end of the exemplary embodiment of FIG. 7A with the valve plug in a closed valve position.

DETAILED DESCRIPTION

Figure 1:
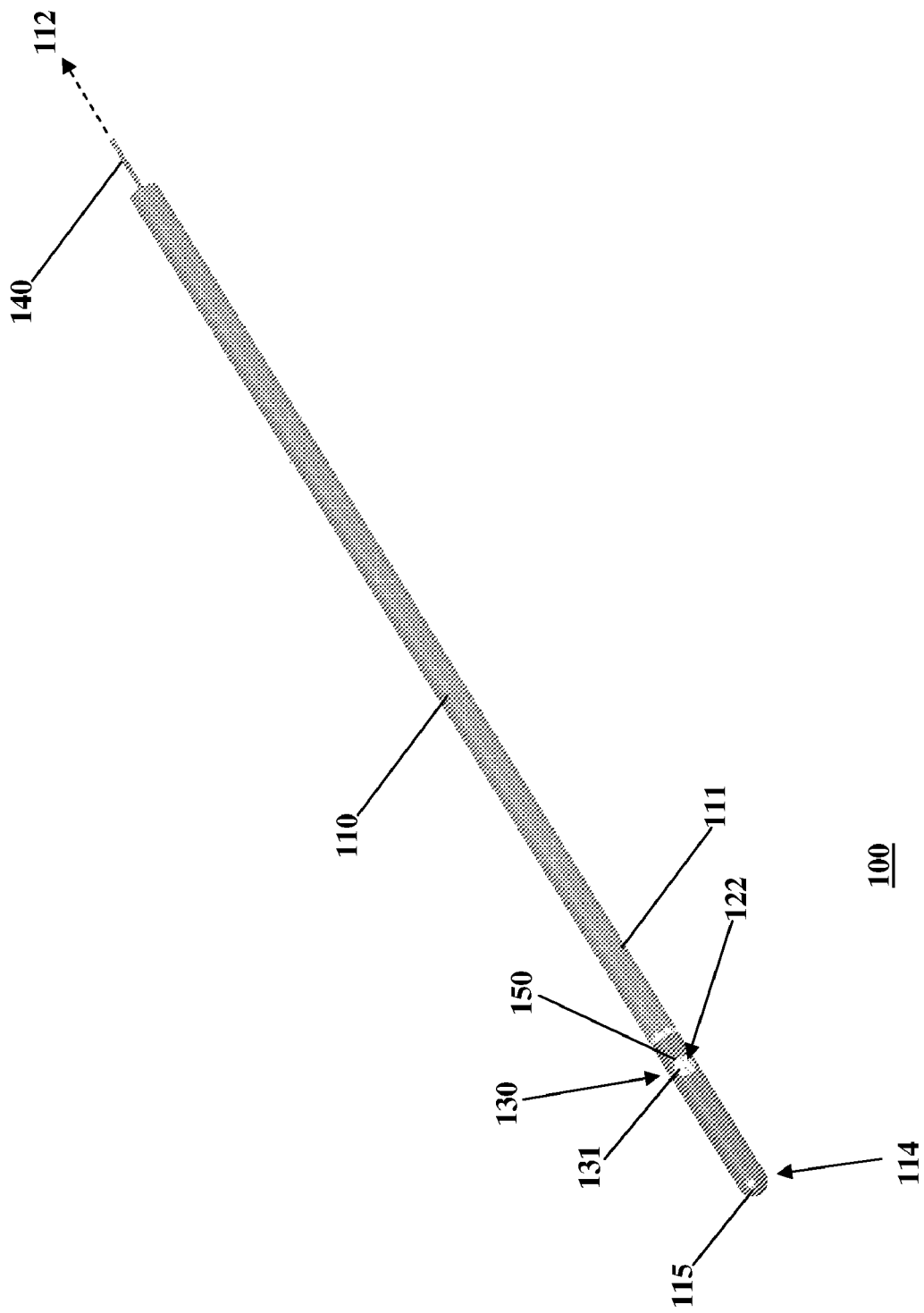
FIG. 1 illustrates a distal end of an exemplary embodiment.

Referring to FIG. 1, an exemplary embodiment of the present invention is generally illustrated as a catheter 100. In particular, as described further below, the catheter 100 may be employed as a central venous catheter for hemodialysis. The catheter 100 has an elongate catheter body 110 which extends from a proximal end 112 to a distal end 114. The catheter 100 is generally flexible to permit positioning within a body passageway, such as a blood vessel. Flexibility, for instance, may be enhanced by incorporating multiple durometer elastomers or polymers within the parts of the catheter 100.

The catheter 100 has a lumen, or interior chamber, within the elongate catheter body 110. The interior chamber (not shown) acts to channel fluid between the proximal end 112 and the distal end 114. The interior chamber has a port, or chamber opening, 122 that passes through a body wall 111 of the catheter body 110. The chamber opening 122 allows the interior chamber to communicate with an area in the body passageway, outside the catheter body 110. The catheter 100 may be operated from the proximal end 112 to guide the distal end 114 to a position in a body passageway. The catheter 100 may deliver fluid to the position in the body passageway through the chamber opening 122. Alternatively, the catheter 100 may draw fluid from the body passageway through the chamber opening 122.

The catheter 100 employs a valve mechanism 130 to control the flow of fluid through the chamber opening 122. As illustrated in FIG. 1, the valve mechanism 130 has a valve wall 131 that acts as a barrier to the flow of fluid into, or from, the catheter 100 when the valve wall 131 is aligned over the chamber opening 122 in a closed valve position. In the closed valve position, the valve mechanism 130 substantially prevents or minimizes the loss of fluid that is intended to be "locked" in the chamber opening 122, an occurrence also known as "lock drop." However, when the valve mechanism 130 is in an open valve position, the valve wall 131 no longer blocks the flow of fluid through the chamber opening 122, and fluid flows between the interior chamber and the area in the passageway outside the catheter 100.

In general, when the valve mechanism 130 is in the closed valve position, a barrier, e.g. the valve wall 131, is in a covered position over the chamber opening 122. On the other hand, when the valve mechanism 130 is in the open valve position, the barrier is in an uncovered position. As used herein, the term barrier refers to a structure, such as the valve wall 131, that substantially prevents or minimizes the flow of fluid.

The distal end 114 of the body 110 forms rounded end, or nose, 115 for the catheter 100. Advantageously, the rounded end 115 reduces blood flow turbulence. Moreover, the shape minimizes contact of the most distal segment, e.g. 10-15 centimeters, of the catheter with native tissue in the body passageway when the catheter is in place.

Figure 2B:
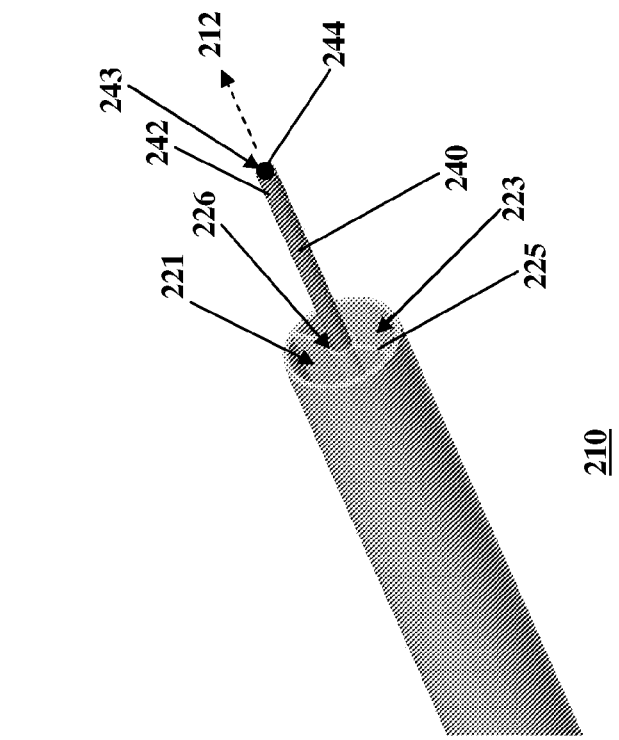
FIG. 2B illustrates a sectional view of a control wire of an exemplary embodiment.
Figure 2A:
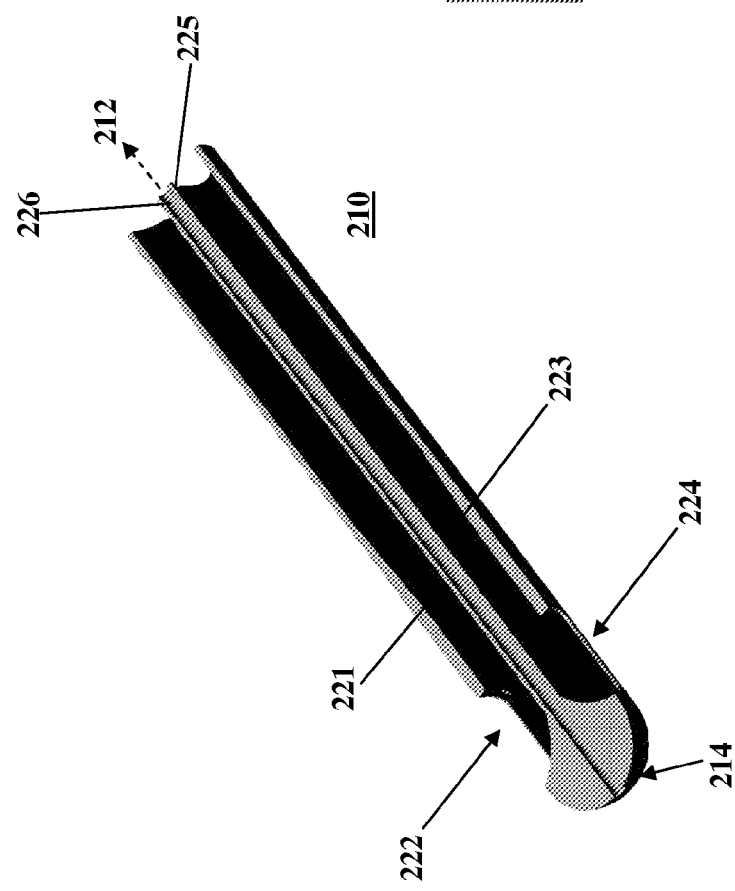
FIG. 2A illustrates a cross-sectional view of a distal end of a catheter body with two interior chambers.

Although the embodiment of FIG. 1 is described in terms of a single interior chamber with chamber opening 122, the cross-sectional view of FIG. 2A demonstrates that other embodiments may employ more than one interior chamber. Accordingly, the elongate catheter body 210 shown in FIG. 2A has two interior chambers 221 and 223. The dividing wall 225 extends longitudinally along the catheter body 210 to separate two halves of the catheter body 210 to define the two interior chambers 221 and 223. The interior chambers 221 and 223 respectively have ports, or chamber openings, 222 and 224. The chamber openings 222 and 223 are near, but spaced from, the distal end 214 of the catheter body 210. It is understood that although the interior chambers 221 and 223 illustrated in FIG. 2A are side-by-side in separate halves of the catheter body 210, other embodiments are not limited to this particular configuration. For instance, an embodiment may employ two lumens that are co-axially arranged.

Although a catheter according to the present invention may use a single interior chamber, the use of the two separate interior chambers 221 and 223 within the elongate body 210, as illustrated in FIG. 2A, is advantageous for applications, such as hemodialysis. In such applications, a first interior chamber is employed for drawing blood to be filtered from the area around the distal end 214 to a dialysis system connected at the proximal end 212. Meanwhile, a second interior chamber is employed for directing filtered blood from the dialysis system to the area around the distal end 214.

Figure 3:
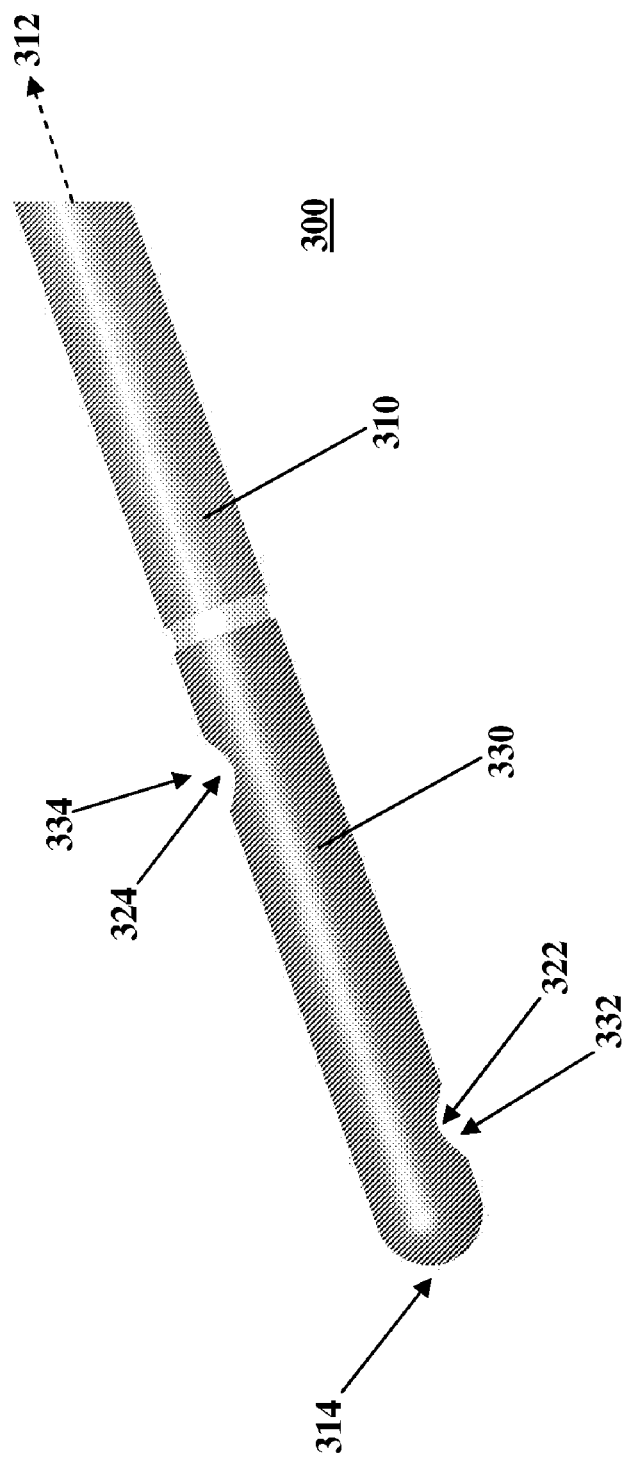
FIG. 3 illustrates a distal end of an exemplary embodiment with chamber openings spaced from the distal end of the catheter body at different distances.

Furthermore, although FIG. 2A illustrates the chamber openings 222 and 224 positioned a similar distance from the distal end 214, other embodiments of the present invention may have chamber openings positioned along the catheter body at different distances from the distal end. For instance, FIG. 3 shows a catheter 300 with chamber openings 322 and 324 for two interior chambers (not shown) that are positioned on the catheter body 310 at two different distances from the distal end 314. Advantageously, the configuration of catheter 300 makes applications, such as hemodialysis, more efficient by permitting blood to be drawn from one section of the blood vessel, and filtered blood to be delivered to a separate section of the blood vessel. In this way, the amount of mixing between filtered blood and non-filtered blood is reduced.

Referring again to FIG. 1, the valve mechanism 130 may include various forms of valve closure members which are operated by a control wire 140 which is attached to the valve mechanism 130 and extends through the elongate body 110 to the proximal end 112. The control wire 140 may be attached by techniques, which include, but are not limited to, welding, overmolding, adhesive bonding, or various types of mechanical interlocking. In addition, spading of the end of the control wire 140 may be employed to create a flatter surface on the control wire 140 to facilitate attachment of the control wire 140 to the valve mechanism 130.

According to an aspect of the present invention, the valve mechanism 130 has a cutting edge 150 that may be employed to cut away a fibrin sheath around the opening 122. The cutting edge 150 may be a thin, smooth sharpened edge. Alternatively, the edge may be textured or serrated to enable the fibrin sheath to be cut or separated into pieces. Moreover, the edge may be straight, curved, or shaped in other ways to promote cutting contact with the fibrin sheath. FIGS. 4A-8B illustrate various embodiments of the valve mechanism in accordance with the present invention.

Figure 4A:
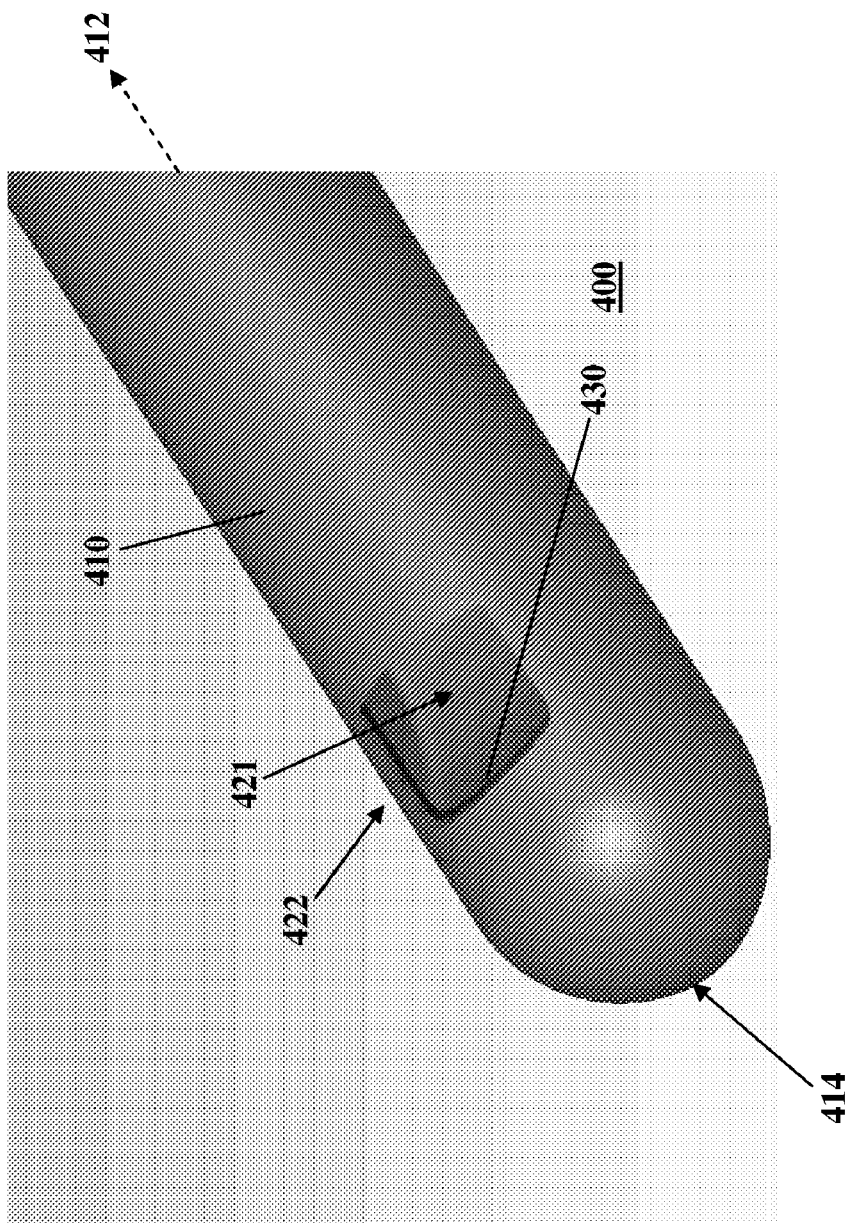
FIG. 4A illustrates a distal end of an exemplary embodiment with a gate in an open valve position.
Figure 4B:
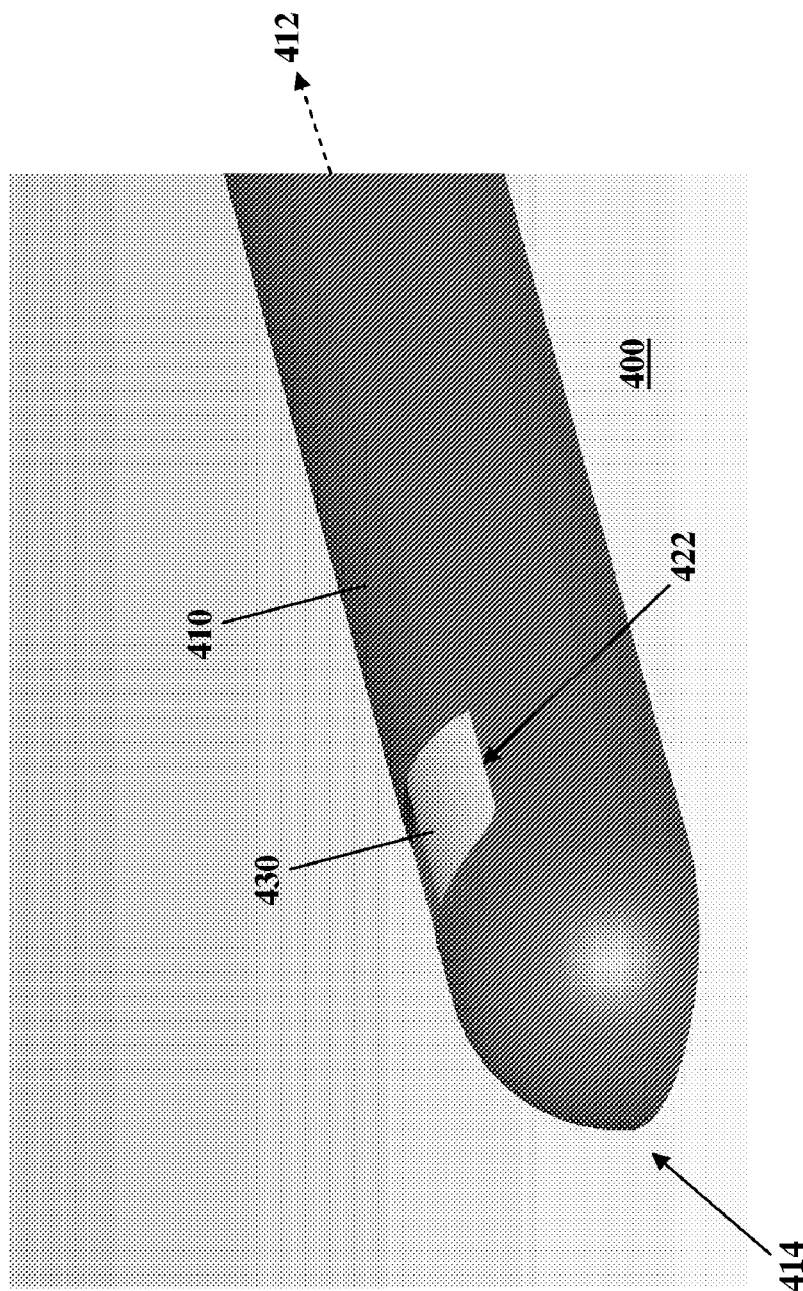
FIG. 4B illustrates the distal end of the exemplary embodiment of FIG. 4A with the gate in a closed valve position.
Figure 4C:
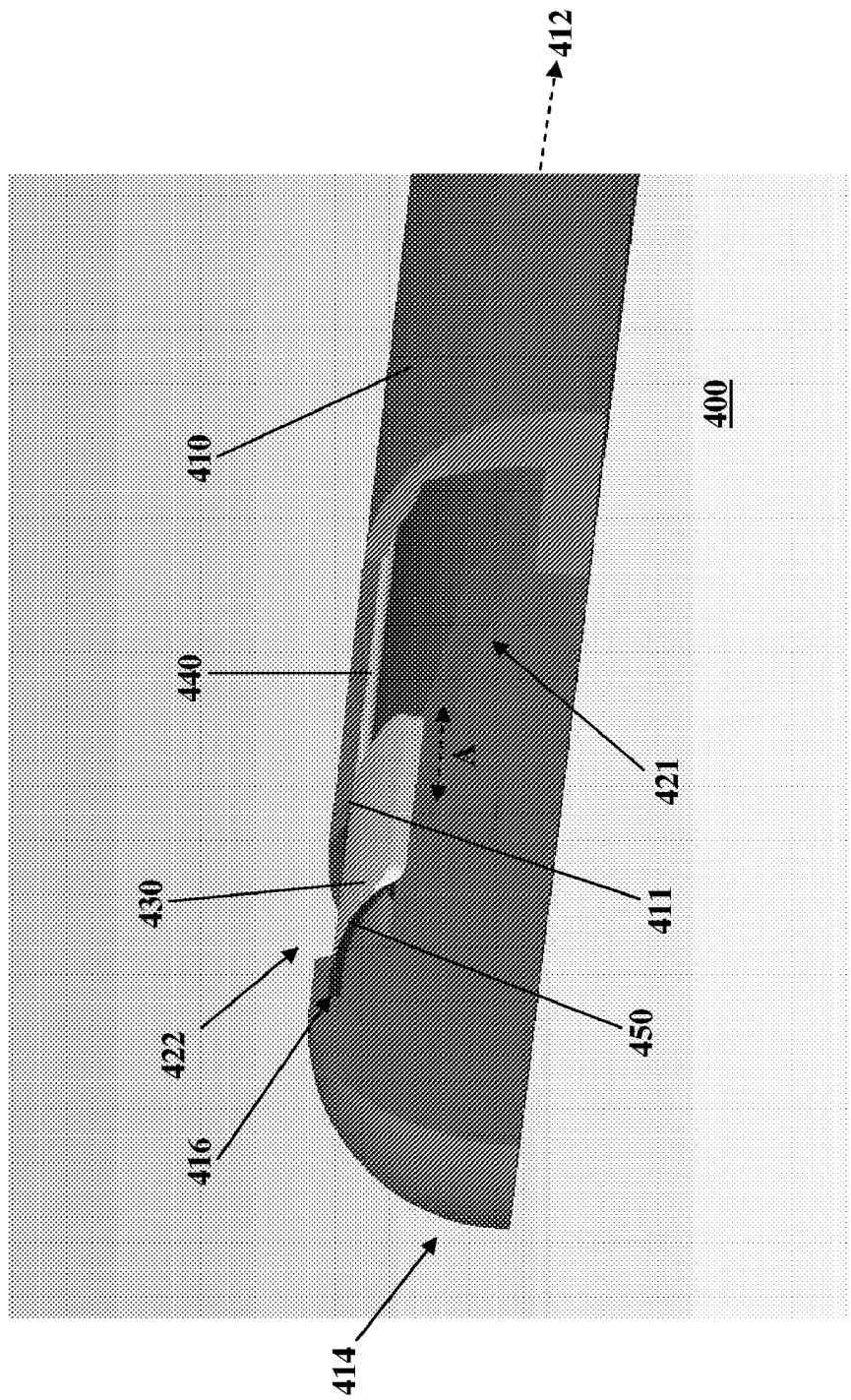
FIG. 4C illustrates a sectional view of the distal end of the exemplary embodiment of FIG. 4A with the gate in a closed valve position.

Referring to FIGS. 4A-C, a catheter 400 has an elongate catheter body 410 with a proximal end 412 and a distal end 414. The catheter 400 has an interior chamber 421 with a chamber opening 422 positioned near the distal end 414.

For a valve mechanism, the catheter 400 employs a gate 430 to control the flow rate of fluid into, or out of, the chamber opening 422. The gate 430 is shown in an open valve position in FIG. 4A. In the open valve position, fluid is permitted to flow between the interior chamber 421 and the area outside the catheter body 410 near the chamber opening 422.

On the other hand, FIG. 4B illustrates the gate 430 in a closed valve position. In the closed valve position, the gate 430 creates a barrier positioned to cover the chamber opening 422, so that flow is substantially prevented between the interior chamber 421 and the area outside the catheter body 410 near the chamber opening 422.

The operation of the gate 430 is described with reference to the sectional view FIG. 4C. The gate 430 is positioned at the chamber opening 422. In addition, the gate 430 is positioned within the interior chamber 421, against the inner surface of the catheter body wall 411. The gate 430 is operated by a control wire 440 which is connected to the gate 430 and extends through the elongate body 410 to the proximal end 412. The control wire 440 is selectively operated to move the gate 430 between the open valve position and the closed valve position. Operation of the control wire 440 moves or slides the gate 430 along the inner surface of the catheter body wall 411 in the direction shown by arrows A along the axial direction of the catheter 400. In particular, because the control wire 440 is attached to the gate 430, the control wire 440 transmits a force to the gate 430 in the axial direction. Referring to FIG. 4C, when the control wire 440 is drawn axially toward the proximal end 412, the control wire 440 draws the gate 430 toward the proximal end 412 to uncover the chamber opening 422. On the other hand, when the control wire 440 is pushed toward the distal end 414, the control wire 440 pushes the gate 430 toward the distal end 414 to cover the chamber opening 422. To ensure that the gate 430 creates a sufficient seal, the leading edge of the gate 430 enters a slot 416 positioned against the inner surface of the body wall 411, as shown in FIG. 4C.

As discussed previously, failure of hemodialysis catheter patency is frequently caused by the accumulation of obstructing thrombus or fibrin at the distal tip of the catheter, particularly after the catheter has been in place for a period of time. Movement of the gate 430 can be employed to achieve disruption and removal of any thrombus or fibrin which has accumulated over the chamber opening 422. However, axial movement of the gate 430 alone may not be sufficient to remove a fibrin sheath which is blocking or restricting flow through the chamber opening 422. As a result, the gate 430 also includes a cutting edge 450 positioned on a side of the gate 430. The cutting edge 450 may be formed by the sharpening of the gate 430 to a thin edge.

In operation, the gate 430 is moved axially to the open valve position so that the gate 430 does not cover with the chamber opening 422. Thus, any fibrin in the area outside the chamber opening 422 is accessible from the interior chamber 421. Using a syringe or other suitable device, a slight vacuum is created in the interior chamber 421 to draw the fibrin sheath through the chamber opening 422. With the fibrin sheath lying in the opening 422, the gate 430 is moved to the closed valve position where the gate 430 covers the chamber opening 422. As the gate 430 moves relative to the chamber opening 422, the cutting edge 450 positioned on the side of the gate 430 passes over the chamber opening 422 and cuts off the fibrin sheath that has been drawn through the opening 422. In particular, the cutting edge 450 acts as a leading edge and contacts the fibrin sheath within the chamber opening 422 as the gate 430 moves toward the distal end 414 into the closed valve position. The cut portions of the fibrin sheath, which now no longer inhibit flow through the opening 422, end up in the interior chamber 421 and may then be removed or flushed from the interior chamber 421 with a syringe or other suitable device.

Although the cutting edge 450 shown in FIG. 4C is positioned on the gate, alternative embodiments may employ a cutting edge positioned on the body wall 411 of the catheter 400 by the chamber opening 422. In such alternative embodiments, the cutting edge on the body wall 411 meets the leading edge of the gate when the gate is in the closed valve position. As the gate moves into the closed valve position, the gate contacts the fibrin sheath in the chamber opening 422 with the leading edge of the gate and pushes the fibrin sheath against the cutting edge on the body wall 411 causing the fibrin sheath to be cut. Accordingly, in general the cutting edges of the valve mechanisms in embodiments of the present invention may be positioned by, or adjacent to, the chamber opening. As such, the cutting edges may be on the catheter body and/or the valve body, such as a gate.

Figure 4D:
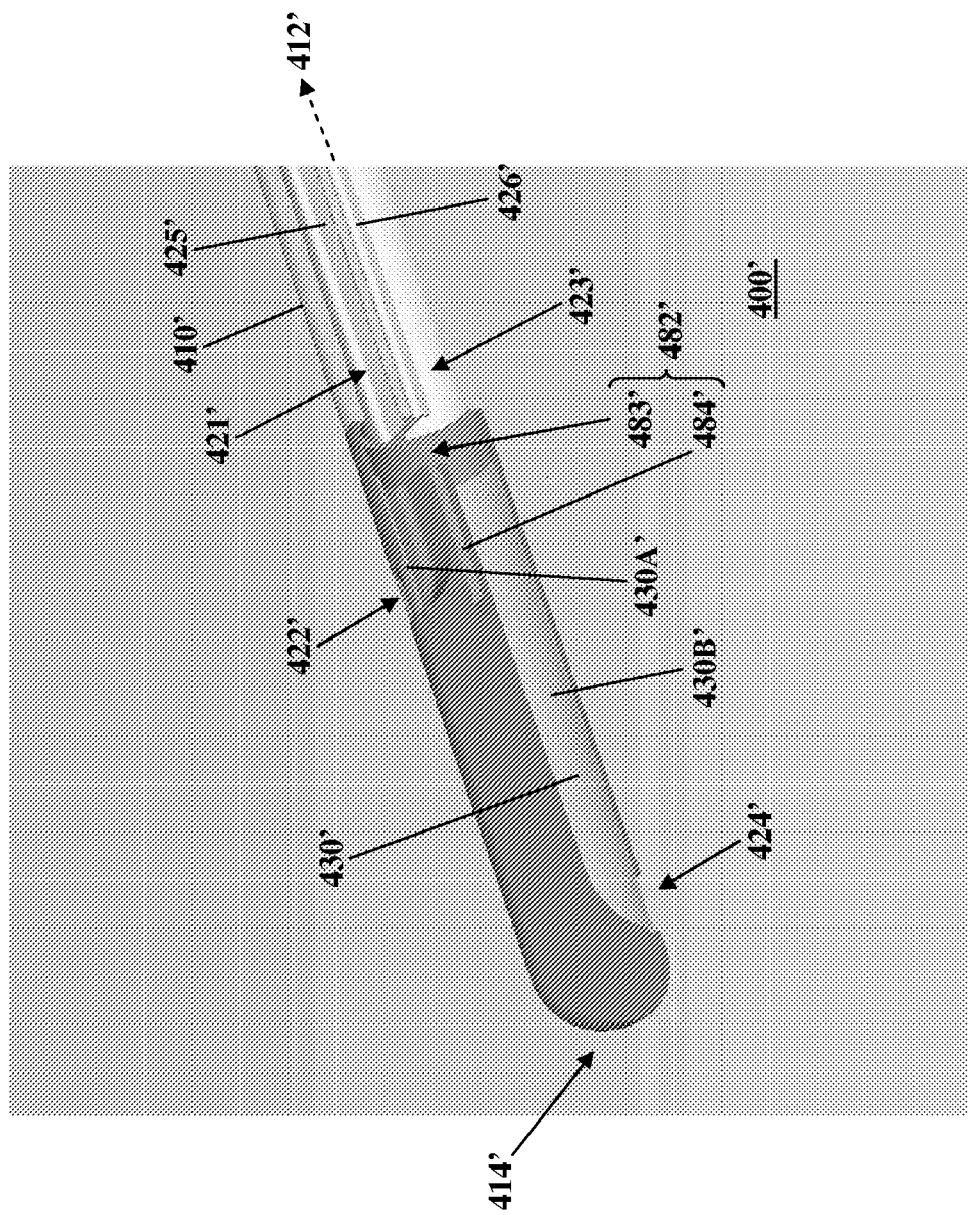
FIG. 4D illustrates a cross-sectional view of an exemplary embodiment with two interior chambers and two respective gates each in a closed valve position.
Figure 4E:
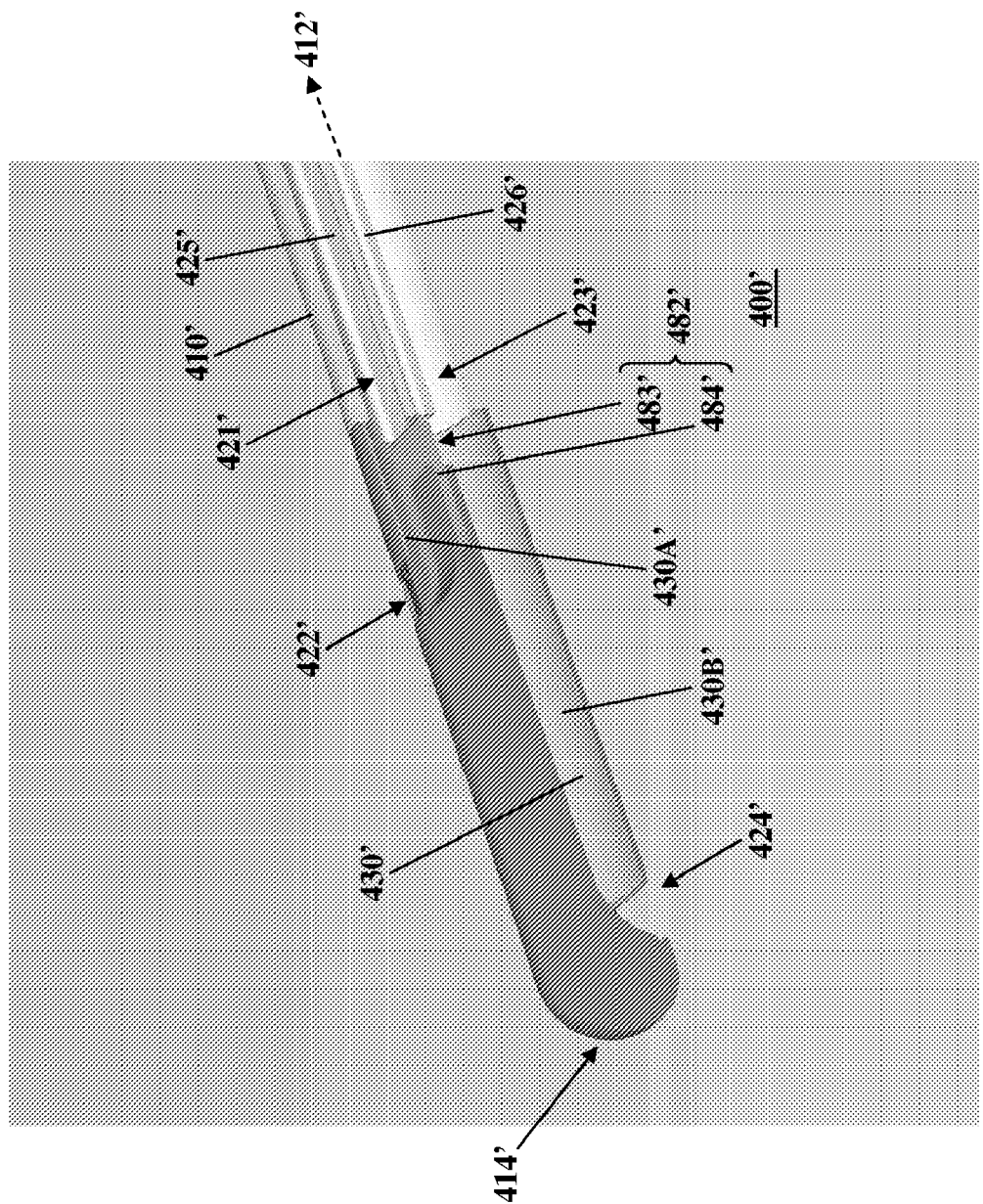
FIG. 4E illustrates a cross-sectional view of the exemplary embodiment of FIG. 4E with the gates each in an open valve position.
Figure 4F:
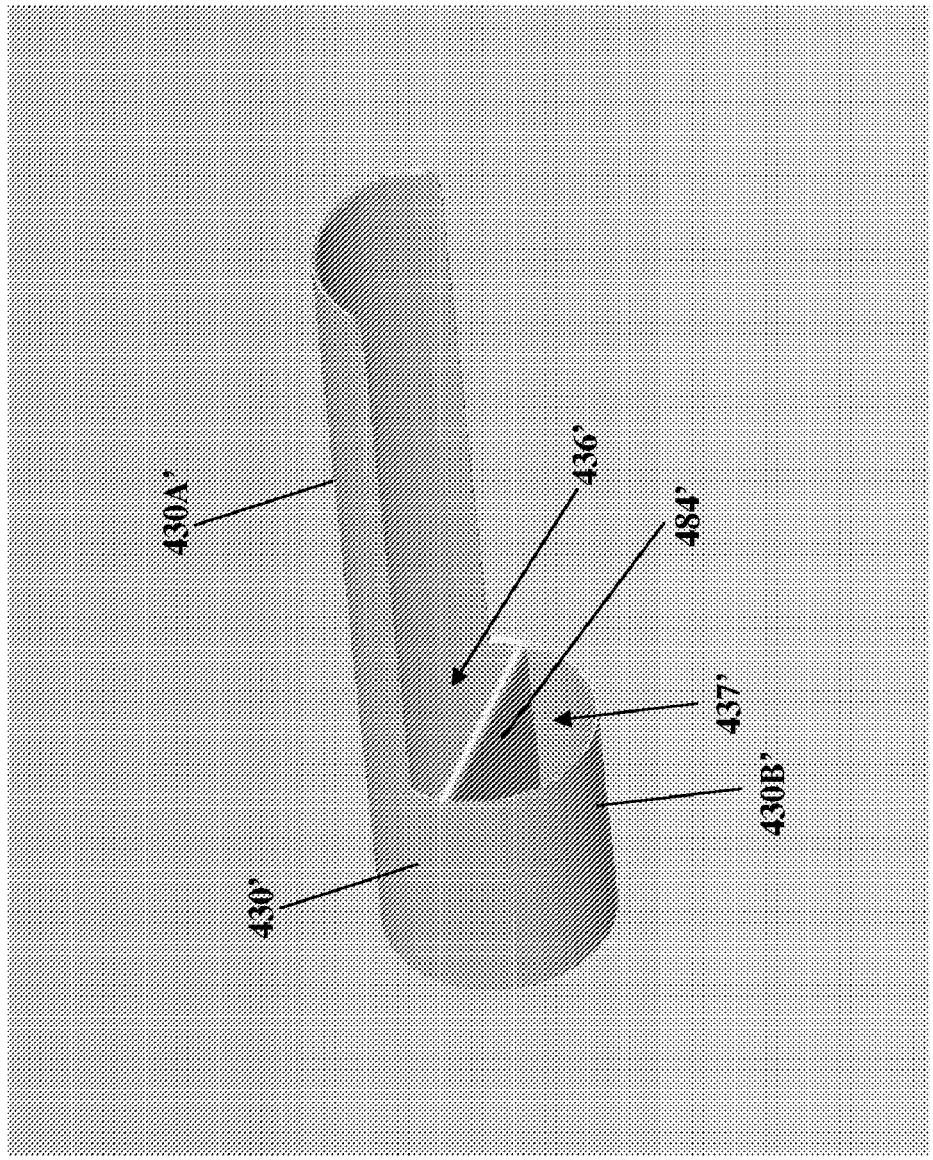
FIG. 4F illustrates an exemplary embodiment of a gate for use with a connecting valve connecting two interior chambers of a catheter body.

While the catheter 400 illustrated in FIGS. 4A-C may have one interior chamber 421 with a single gate 430, the alternative embodiment shown in FIGS. 4D-F illustrates a catheter 400' that has two interior chambers 421' and 423' and two gates 430A' and 430B' to control the flow of fluid through the chamber openings 422' and 424'. The interior chambers 421' and 423' extend from a proximal end 412' to a distal end 414'. In addition, the interior chambers 421' and 423' have the chamber openings 422' and 424', respectively, positioned near the distal end 414'. However, the chamber openings 422' and 424' are positioned at different distances from the distal end 414'. FIG. 4D shows the gates 430A' and 430B' each in a closed valve position. On the other hand, FIG. 4E shows the gates 430A' and 430B' each in an open valve position. As more clearly shown in FIG. 4F, the gates 430A' and 430B' may be part of the same body 430'. As such, gates 430A' and 430B' move together with operation of body 430'. In particular, in the present embodiment, the gates 430A' and 430B' move together from the closed valve positions, shown in FIG. 4D, to the open valve positions, shown in FIG. 4E, when the body 430' is drawn longitudinally by corresponding movement of the control wire (not shown) toward the proximal end 412'. Conversely, the gates 430A' and 430B' move together from the open valve positions to the closed valve positions when the body 430' is driven longitudinally by corresponding movement of the control wire in the reverse direction toward the distal end 414'. Further details regarding body 430' are provided hereinbelow. Although the embodiments shown in FIGS. 4A-F have gates that move longitudinally, it is understood that the gate in alternative embodiments may move in another direction, e.g. along a plane substantially transverse to a longitudinal line of the catheter body.

Figure 5A:
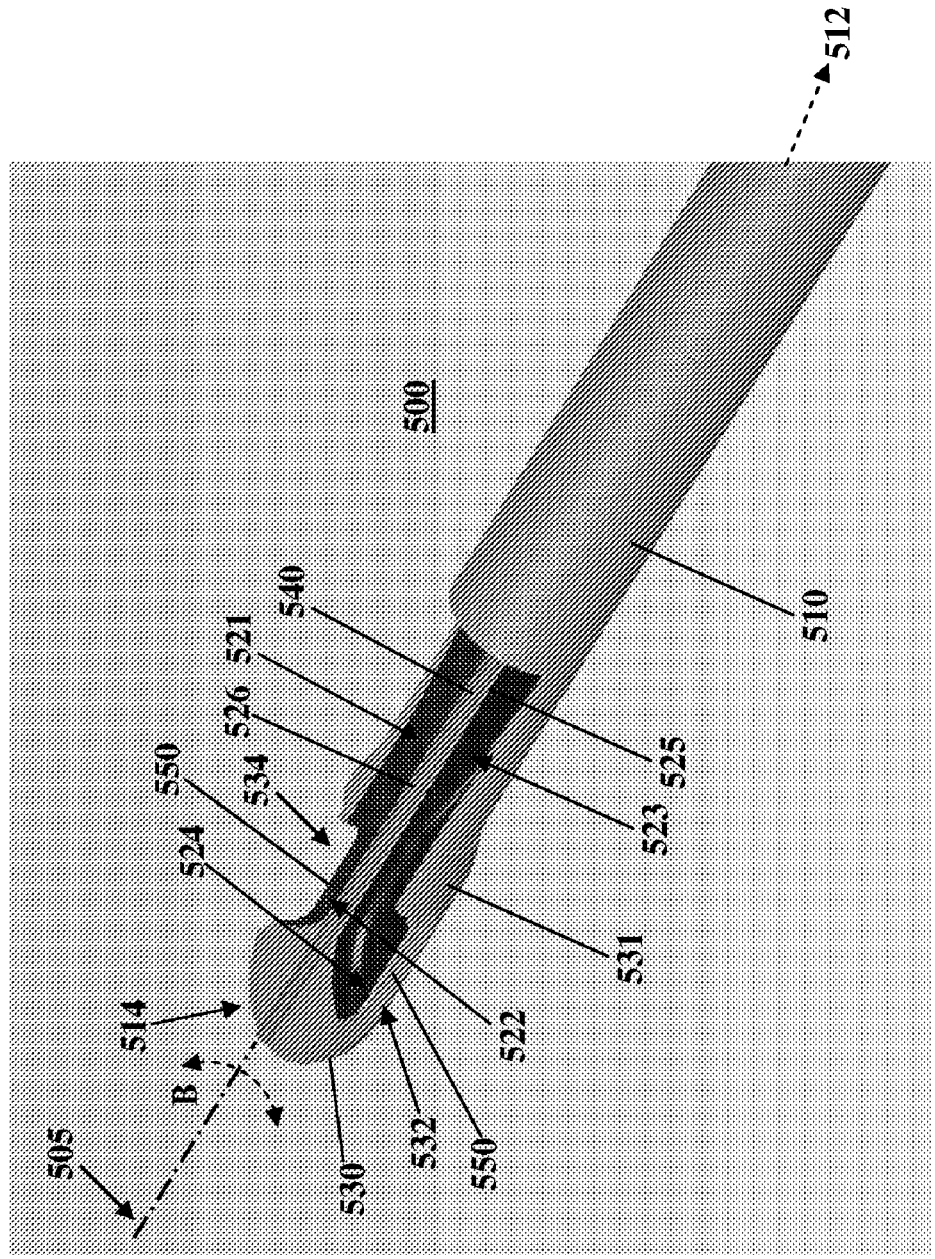
FIG. 5A illustrates a sectional view of a distal end of an exemplary embodiment with a rotating cap-shaped valve in an open valve position.
Figure 5B:
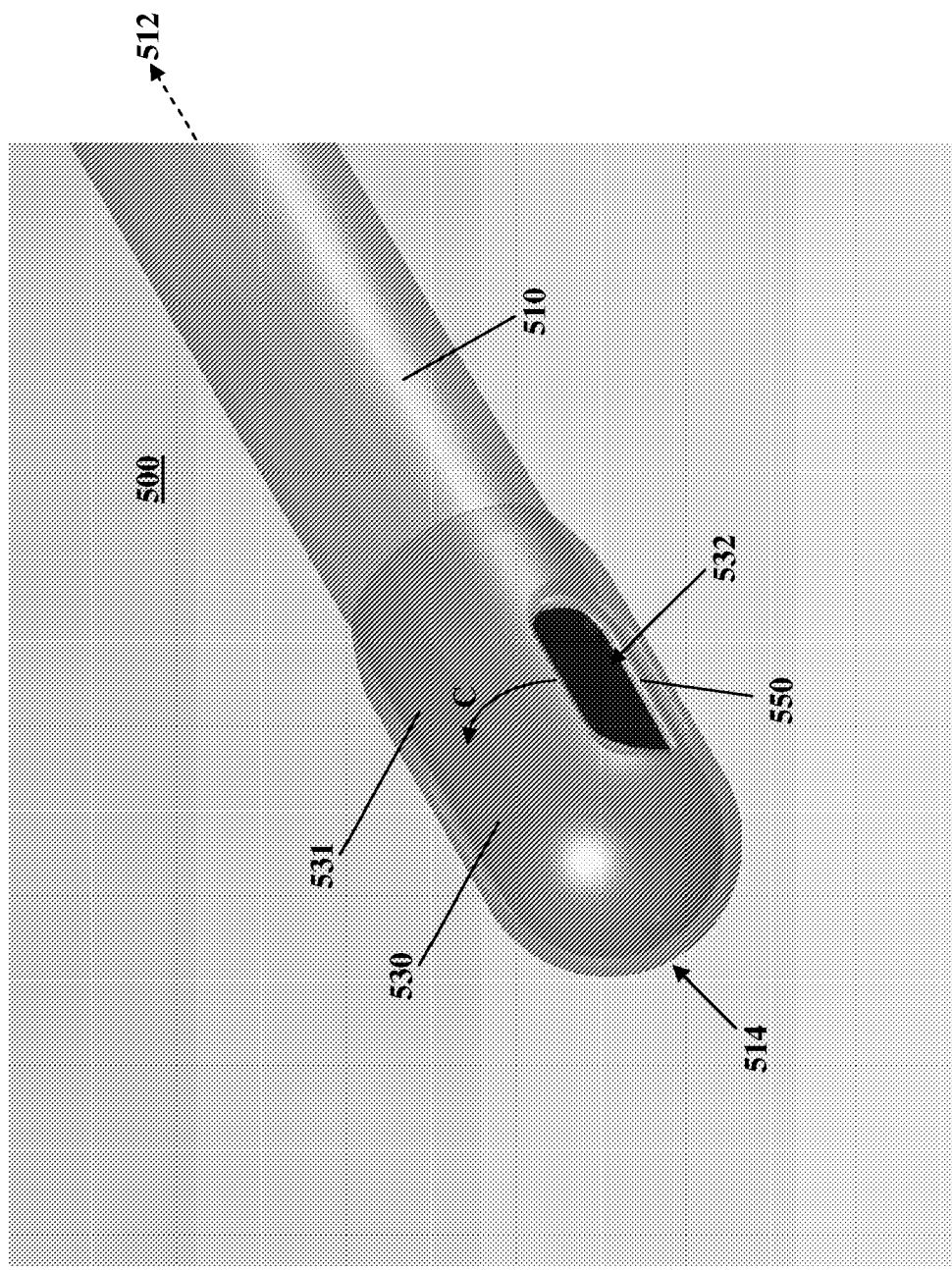
FIG. 5B illustrates the distal end of the exemplary embodiment of FIG. 5A with the cap-shaped valve in a closed valve position.

FIGS. 5A-B illustrate an alternative to the gate 430 described previously. The exemplary embodiment of FIGS. 5A-B employs a cap-shaped valve 530. Referring to FIG. 5A, a catheter 500 has a cap 530 at the distal end 514 of an elongate catheter body 510. The catheter body 510 has two interior chambers 521 and 523. A dividing wall 525 extends longitudinally along the catheter body 510 to separate two halves of the catheter body 520 and define the two interior chambers 521 and 523. The interior chamber 521 has a chamber opening 522 near the distal end 514, and similarly, the interior chamber 523 has a chamber opening 524 near the distal end 514. As illustrated in FIG. 5A, the cap 530 has two cap openings 532 and 534, which are defined by a cap wall 531 and which are aligned with the chamber openings 522 and 524, respectively. With the open valve position of the cap 530 shown in FIG. 5A, the chamber opening 522 and the cap opening 532 open the interior chamber 521 to the area outside the cap opening 532, and fluid is able to flow between the interior chamber 521 and the area outside the cap opening 532. Similarly, the chamber opening 524 and the cap opening 534 open the interior chamber 523 to the area outside the cap opening 534, and fluid is also able to flow between the interior chamber 523 the area outside the cap opening 534.

The cap 530 moves from the open valve position to a closed valve position by rotating relative to the catheter body 510 about a longitudinal line 505. The rotation may occur in one of the directions depicted by the arrows B in FIG. 5A. The cap openings 532 and 534 are defined by a cap wall 531. When the cap openings 532 and 534 are not aligned with the chamber openings 522 and 524, respectively, portions of the cap wall 531 act as barriers positioned to cover the chamber openings 522 and 524. When the cap openings 532 and 534 and the chamber openings 522 and 524 are completely misaligned, the chamber openings 522 and 524 are completely covered. With the chamber openings 522 and 524 blocked by the cap wall 531, fluid flow is substantially prevented between the interior chambers 521 and 523 and the passageway outside the catheter 500.

FIG. 5A also illustrates a control wire 540 that is connected to an inner portion of the cap 530 at the distal end 514. The control wire extends from the distal end 514 to the proximal end 512. The control wire 540 is operated to move the cap 530 between the open valve position and the closed valve position. In particular, the rotation of the control wire 540 transmits a rotational force to the cap 530 to open or close the chamber openings 522 and 524 by virtue of the control wire 540 being attached, preferably to the center of the cap 530.

As further illustrated in FIG. 5A, the control wire 540 is positioned in a control wire channel 526, which extends from the proximal end 512 to the distal end 514 within the dividing wall 525. The control wire channel 526 is dimensioned to permit rotation of the control wire 540, and may accommodate the use of a lubricant to facilitate motion of the control wire while substantially preventing any escape of the lubricant from the channel 526.

Referring again to FIG. 2A, a further example of a control wire channel is illustrated. In particular, the control wire channel 226 is positioned within a longitudinal dividing wall 225 of the catheter body 210. FIG. 2B shows a sectional view of the catheter body 210, where the dividing wall 225 divides the catheter body into two halves to define the interior chambers 221 and 223. The control wire 240 passes through the control wire channel 226 formed within the dividing wall 225. As shown further in FIG. 2B, the control wire 240 may have a tube-shaped body 242 with a septum valve (not shown) at both proximal and distal ends. A guide wire channel 243 is formed in the tube-shaped body 242. As such, in order to facilitate catheter positioning, the implanting physician extends a guide wire 244 to a location in a body passageway. The guide wire 244 is then positioned within the guide wire channel 243 through the center of the tube body 242, and the catheter body 210 is guided along the guide wire 244 to the location in the body passageway. Once the catheter body 210 is positioned in the body passageway, the guide wire 244 can be extracted. Upon guide wire removal, a permanent plug may be inserted into the proximal end of the tube body 242 to close the guide wire channel 243 and prevent air embolism and/or blood loss. To further facilitate proper positioning of the catheter body 210 within the body passageway, the guide wire 244 may include, near the distal end of the guide wire 244, a centering mechanism, such as a plurality of elongate legs defining an expanding centering basket.

As discussed previously, failure of hemodialysis catheter patency is frequently caused by the accumulation of obstructing thrombus or fibrin at the distal tip of the catheter, particularly after the catheter has been in place for a period of time.

In some instances, mere rotation of the cap 530 can be employed to achieve disruption and removal of any thrombus or fibrin which has accumulated over the cap 530. However, merely rotating the cap 530 may not be sufficient to remove a fibrin sheath which is blocking or restricting flow through the chamber openings 522 and 524. As a result, the cap 530 also includes cutting edges 550 positioned on the inner edge of the cap openings 532 and 534. For example, a cutting edge 550 on the cap opening 532 is shown in closer detail in FIG. 5B. The cutting edge 550 may be formed by the sharpening of the cap wall 531 of the cap 530 to a thinner edge at the cap opening 532.

In operation, the cap 530 is rotated to the open valve position in order to bring the cap openings 532 and 534 into alignment with the chamber openings 522 and 524, respectively. Thus, any fibrin in the area outside the cap openings 532 and 534 is accessible from the interior chambers 521 and 523. Using a syringe or other suitable device, a slight vacuum is created in the chambers 521 and 523 to draw the fibrin sheath through the cap openings 532 and 534 and the chamber openings 522 and 524, respectively. With the fibrin sheath lying in these openings, the cap 530 is rotated to the covered position to move the cap openings 532 and 534 out of alignment with the chamber openings 522 and 524. As the openings 532 and 534 rotate relative to the chamber openings 522 and 524, the cutting edges 550 positioned on the inner edge of the cap openings 532 and 534 pass over the chamber openings 522 and 524 and cut off the fibrin sheath that has been drawn through these openings. For example, as shown in FIG. 5B, the cutting edge 550 acts as a leading edge as the cap 530 moves in the direction of arrow C into the closed valve position. In this way, the sharpened part is guided into contact with the fibrin sheath. The cut portions of the fibrin sheath, which now no longer inhibit flow through the openings, end up in the interior chambers 521 and 523 and may then be removed or flushed from the interior chambers 521 and 523 with a syringe or other suitable device.

Figure 6A:
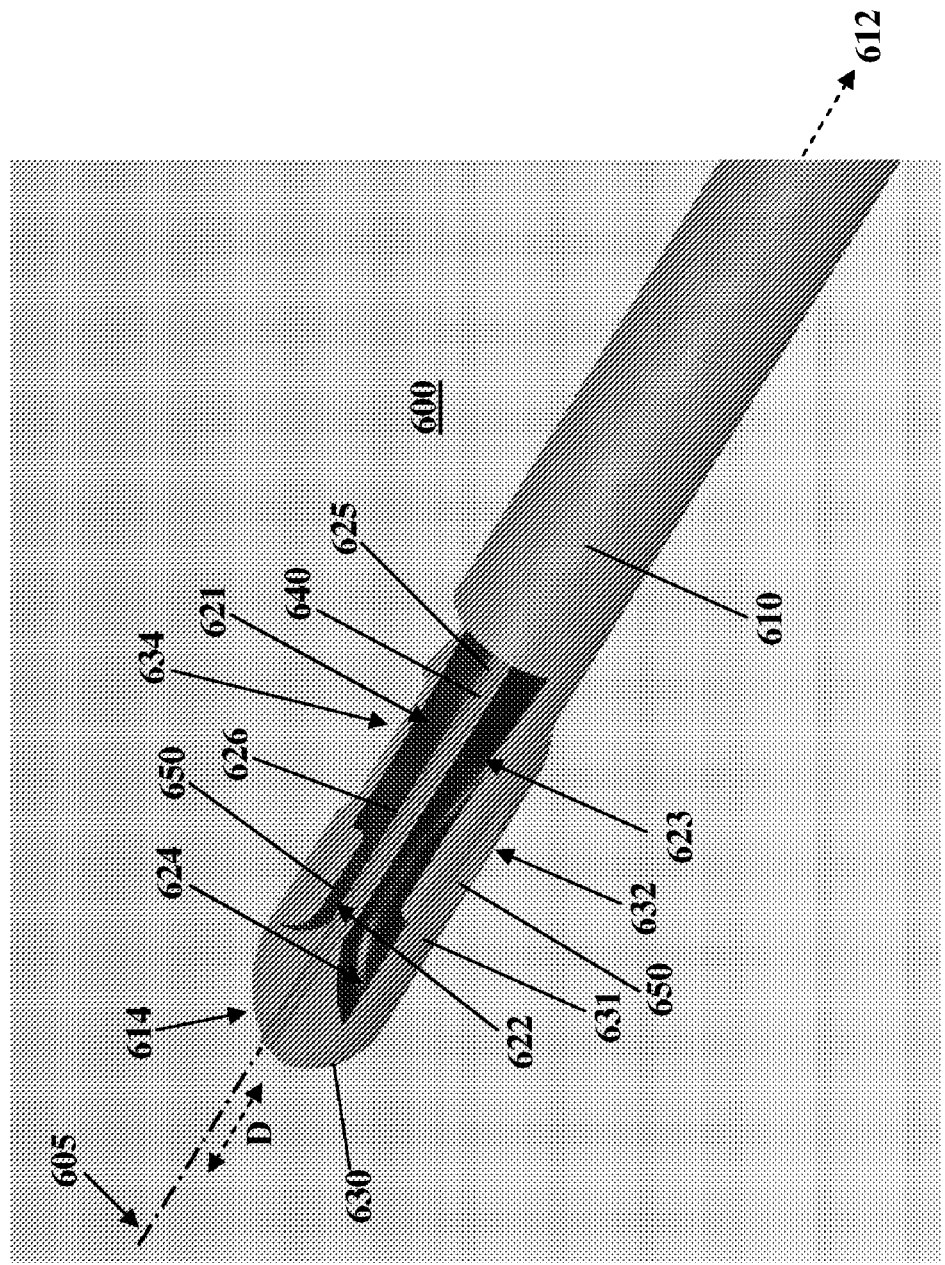
FIG. 6A illustrates a sectional view of a distal end of an exemplary embodiment with an axially translating cap-shaped valve in an open valve position.
Figure 6B:
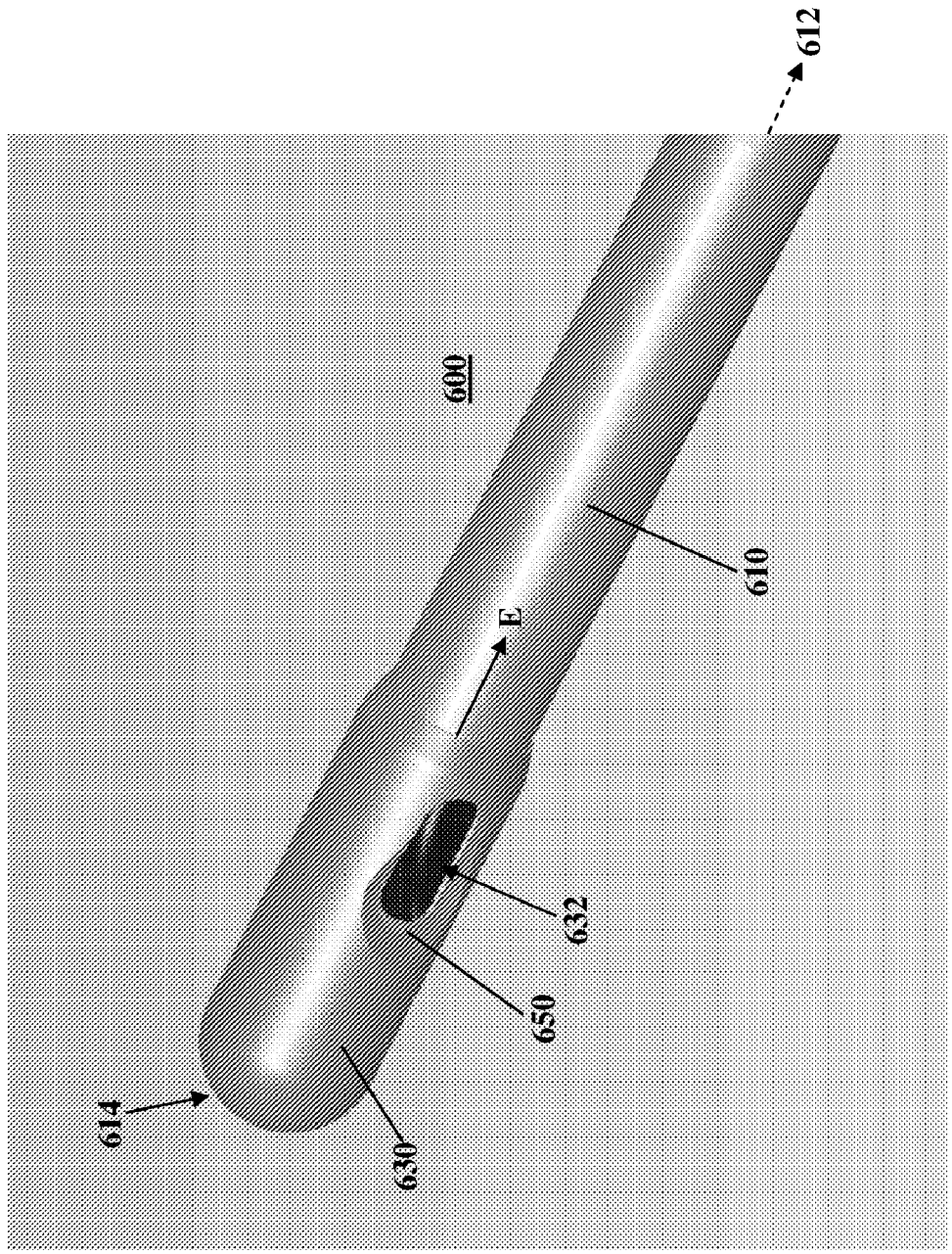
FIG. 6B illustrates the distal end of the exemplary embodiment of FIG. 6A with the cap-shaped valve in a closed valve position.

A further embodiment of a valve mechanism is illustrated in FIGS. 6A-B. The embodiment provides a catheter 600 which employs the cap 630 to act as the valve mechanism to control the flow of fluid during operation of the catheter 600. The cap 630 is mounted on the distal end 614 of an elongate catheter body 610. An interior dividing wall 625 extending longitudinally along the catheter body 610 defines two interior chambers 621 and 623. The interior chamber 621 has a chamber opening 622 near the distal end 614, and similarly, the interior chamber 623 has a chamber opening 624 near the distal end 614. The cap 630 has two cap openings 632 and 634 which are defined by cap wall 631. As illustrated in FIG. 6A, the cap openings 632 and 634 are not aligned with the chamber openings 622 and 624, so that the portions of the cap wall 631 act as barriers to cover the chamber openings 622 and 624. The orientation of the cap 630 shown in FIG. 6A corresponds with a closed valve position.

Although the catheter 600 uses a cap as a valve mechanism, the catheter 600 differs from the catheter 500 described above. When the cap 630 moves between the open and closed valve positions, it moves, or translates, axially along the longitudinal axis 605, instead of rotating like the cap 530. In other words, the cap 630 moves in the direction of the arrows D shown in FIG. 6A.

Accordingly, in order to move from the closed valve position to the open position, the cap 630 moves relative to the elongate catheter body 610 in the axial direction toward the distal end 614 until the cap openings 632 and 634 align with the chamber openings 622 and 624, respectively. In this open valve position, fluid is able to flow between the interior chamber 621 and the area outside the cap opening 632. Similarly, fluid is able to flow between the interior chamber 623 and the area outside the cap opening 634. To achieve the closed valve position again, the cap 630 is moved in the axial direction toward the proximal end 612 until the cap openings 632 and 634 are no longer aligned with the chamber openings 622 and 624, respectively.

The cap 630 is controlled by a control wire 640 that is connected to an inner portion of the cap 630 at the distal end 614. The control wire 640 is positioned within a control wire channel 626 in the dividing wall 625 and extends from the distal end 614 to the proximal end 612. The control wire 640 is operated to move the cap 630 between the open valve position and the closed valve position. In particular, the control wire 640 transmits an axial force to the cap 630 to open or close the chamber openings 622 and 624.

Axial movement of the cap 630 can be employed to achieve disruption and removal of any thrombus or fibrin which has accumulated over the cap 630. However, if this axial movement of the cap 630 alone is not be sufficient to remove a fibrin sheath, cutting edges 650 positioned on the inner edge of the cap openings 632 and 634 may be employed. For example, a cutting edge 650 on the cap opening 632 is shown in closer detail in FIG. 6B. The cutting edge 650 is formed by the sharpening of the cap wall 631 of the cap 630 to a thinner edge at the cap opening 632.

In operation, the cap 630 is moved axially to the open valve position in order to bring the cap openings 632 and 634 into alignment with the chamber openings 622 and 624, respectively. Using a syringe or other suitable device, a slight vacuum is created in the chambers 621 and 623 to draw the fibrin sheath through the cap openings 632 and 634 and the chamber openings 622 and 624, respectively. With the fibrin sheath lying in these openings, the cap 630 is moved axially to the closed valve position to move the cap openings 632 and 634 out of alignment with the chamber openings 622 and 624. As the openings 632 and 634 rotate relative to the chamber openings 622 and 624, the cutting edges 650 positioned on the inner edge of the cap openings 632 and 634 pass over the chamber openings 622 and 624 and cut off the fibrin sheath that has been drawn through these openings. For example, as shown in FIG. 6B, the cutting edge 650 acts as a leading edge as the cap 630 moves in the direction of arrow E into the closed valve position. In this way, the sharpened part is guided into contact with the fibrin sheath. The cut portions of the fibrin sheath, which now no longer inhibit flow through the openings, end up in the interior chambers 621 and 623 and may then be removed or flushed from the interior chambers 621 and 623 with a syringe or other suitable device.

In the manner previously noted, the cap may be implemented with chamber openings that are positioned at different distances from the distal end. In this regard, the embodiment of FIG. 3 provides a catheter 300 with chamber openings 322 and 324 for two interior chambers, the openings being positioned at two different distances from the distal end 314. The cap 330 may either rotate or move axially to move between the closed valve position and the open valve position.

In addition to the gate valve and the cap-shaped valves described above, other valve mechanisms may be employed with the present invention. For instance, FIGS. 7A-B illustrate a catheter body 700 that has a single interior chamber 721 that has an enlarged chamber opening 722 at the distal end 714 of the catheter body 710. Of course, the catheter body 700 may alternatively be implemented to have multiple coaxial chambers sharing the same opening 722 in other embodiments. The chamber opening 722 is selectively opened or closed by the axial movement of a valve plug 730 connected to a control wire 740. The control wire 740 may be operated from a proximal end 712, as described further below. FIG. 7A shows the catheter 700 with the valve plug 730 in an open valve position, while FIG. 7B shows the catheter 700 in a closed valve position. The valve plug 730 is formed with a rear section 732 that tapers to a smaller dimension at the rear. The rear section 732 fits into and closes the chamber opening 722. A rounded forward section 735 forms a bullet shaped nose for the catheter body 710. Advantageously, the rounded section 735 reduces blood flow turbulence. Moreover, the shape minimizes contact of the most distal segment of the catheter with native tissue when the catheter is in place.

The valve plug 730 may be moved back and forth relative to the chamber opening 722 to disrupt any thrombus or fibrin which has accumulated over the distal end 714 of the catheter body 710. A cutting edge 750 is employed along the edge of the chamber opening 722 to cut the fibrin sheath. To cut the fibrin sheath, the valve plug 730 is moved into the closed valve position after the fibrin sheath has been drawn into the interior chamber 721 with a slight vacuum.

Figure 8A:
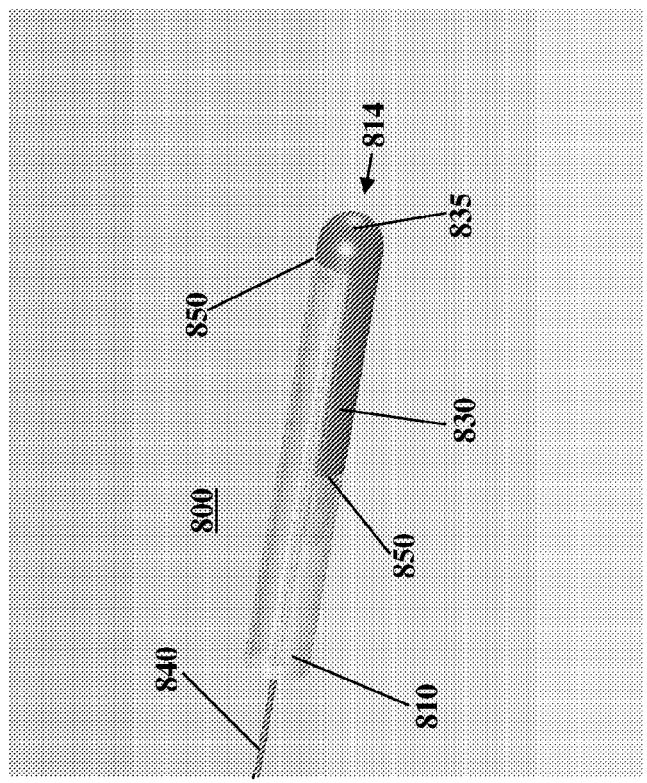
FIG. 8A illustrates the distal end of an exemplary embodiment with two interior chambers and a valve plug in an open valve position.
Figure 8B:
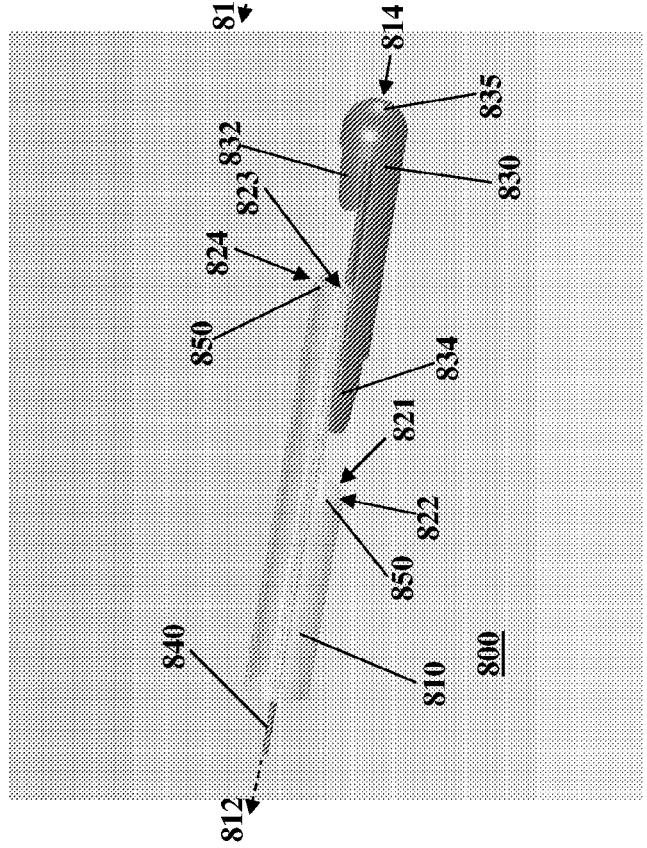
FIG. 8B illustrates the distal end of the exemplary embodiment of FIG. 8A with the valve plug in a closed valve position.

The catheter 800 of FIGS. 8A-B is similar to catheter 700 because it also employs a valve plug 830. However, the catheter 800 has two side-by-side interior chambers 821 and 823 with chamber openings 822 and 824, respectively. As such, the valve plug 830 has two rear sections 832 and 834 that taper to a smaller dimension at the rear. The rear sections 832 and 834 fit into and close the chamber openings 822 and 824, respectively. As illustrated in FIG. 8A, the chamber openings 822 and 824 are positioned at different distances from the distal end 814 of the catheter 800. Therefore, the valve plug 830 is shaped accordingly so that the tapered rear surface 834 extends farther from the distal end 814 than the tapered rear surface 832. However, the valve plug 830 maintains a rounded front section 835 which advantageously forms a bullet shaped nose for the catheter body 810.

The chamber openings 822 and 824 are selectively opened or closed by the axial movement of a valve plug 830 connected to a control wire 840. The control wire 840 may be operated from a proximal end 812, as described further below. FIG. 8A shows the valve plug 830 in the open valve position, while FIG. 8B shows the valve plug 830 in the closed valve position. The valve plug 830 may be moved back and forth relative to the chamber openings 822 and 824 to disrupt any thrombus or fibrin which has accumulated in the area of the chamber openings 822 and 824. Moreover, cutting edges 850 may be employed along the edges of the chamber openings 822 and 824 to cut the fibrin sheath. To cut the fibrin sheath, the valve plug 830 is moved into the closed valve position after the fibrin sheath has been drawn into the interior chambers 821 and 823 with a slight vacuum.

Figure 9A:
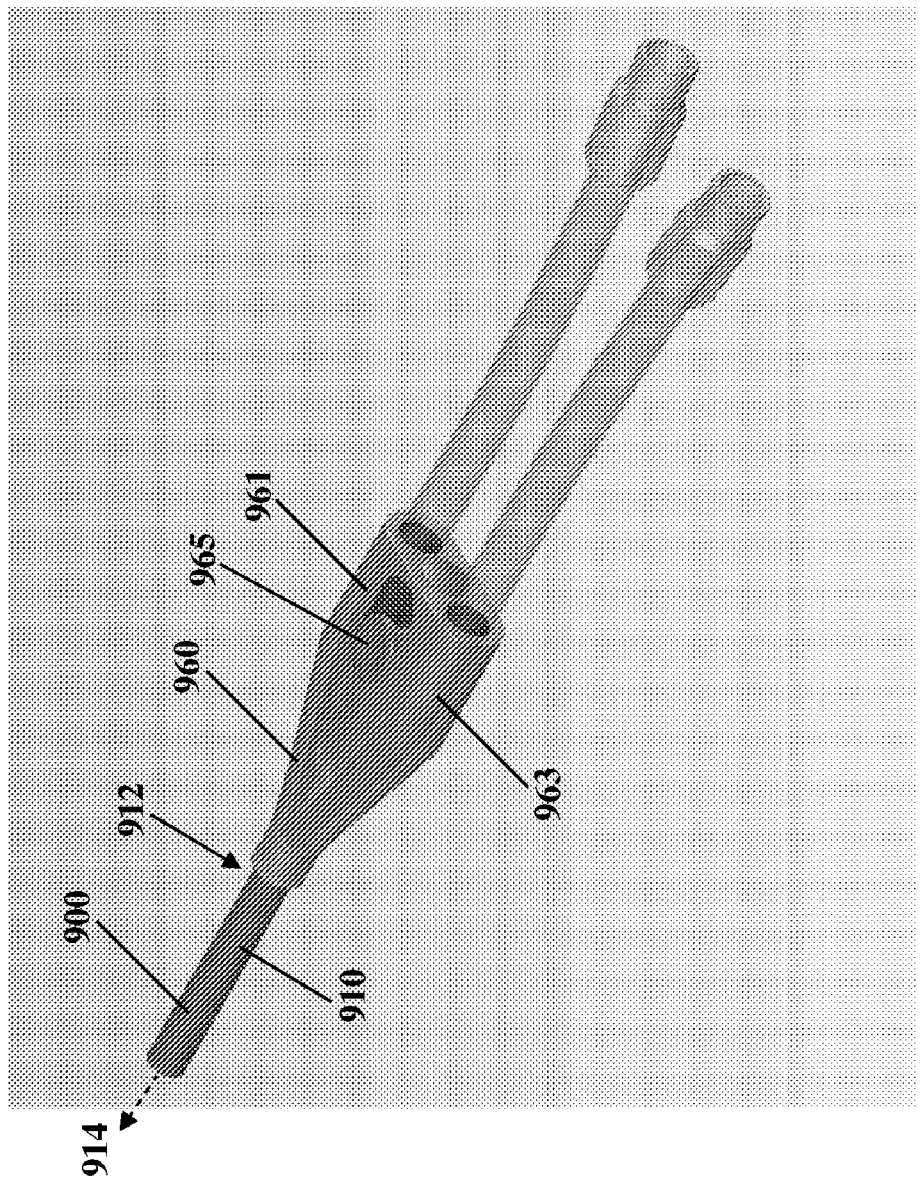
FIG. 9A illustrates an exemplary embodiment with a hub at the proximal end.
Figure 9B:
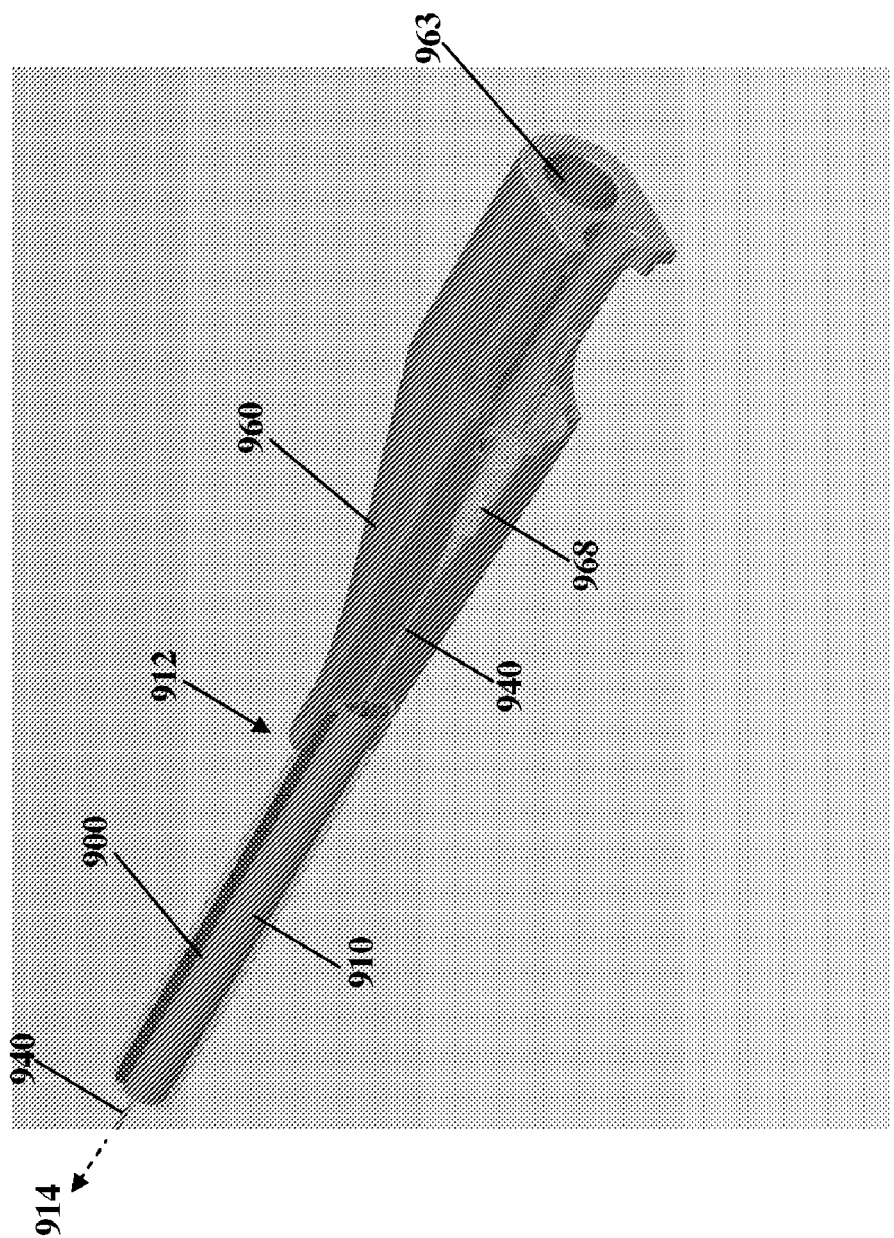
FIG. 9B illustrates a sectional view of the exemplary embodiment of FIG. 9A.

As described previously, each of the valve mechanisms of the exemplary embodiments above may be selectively actuated by a control wire that extends from the valve mechanism at the distal end to the proximal end of the catheter. The control wire may be operated by the operator from the proximal end of the catheter. Accordingly, FIGS. 9A-B illustrate a proximal hub 960 which is secured to the proximal end 912 of a catheter 900. The catheter 900 has two interior chambers (not shown) extending from the distal end 914 to the proximal end 912 of the catheter 900. The proximal hub 960 includes a fluid port 961 in communication with one interior chamber and a fluid port 963 in communication with the other interior chamber. From the interior chambers, the fluid ports 961 and 963 may lead to a supply of fluid to be introduced into the interior chambers, or may lead to a receiving system to deposit fluid drawn from the body passageway.

Moreover, the proximal hub 960 has a control mechanism 965, such as a button, that is connected to, and operates, the control wire 940, as shown in FIG. 9B. The operator moves the control button 965 to cause corresponding movement of the control wire 940. To maintain a sufficient seal between the control wire 940 and the hub 960, the control wire 940 and hub 960 are attached to a rolling membrane 968. The rolling membrane 968 acts as an inverting bellow which allows the control wire 940 to move, particularly in the axial direction, while maintaining a seal between the control wire 940 and the hub 960. The rolling membrane may be formed from a flexible material, such as silicone, polyurethane, or other elastomer.

Figure 10:
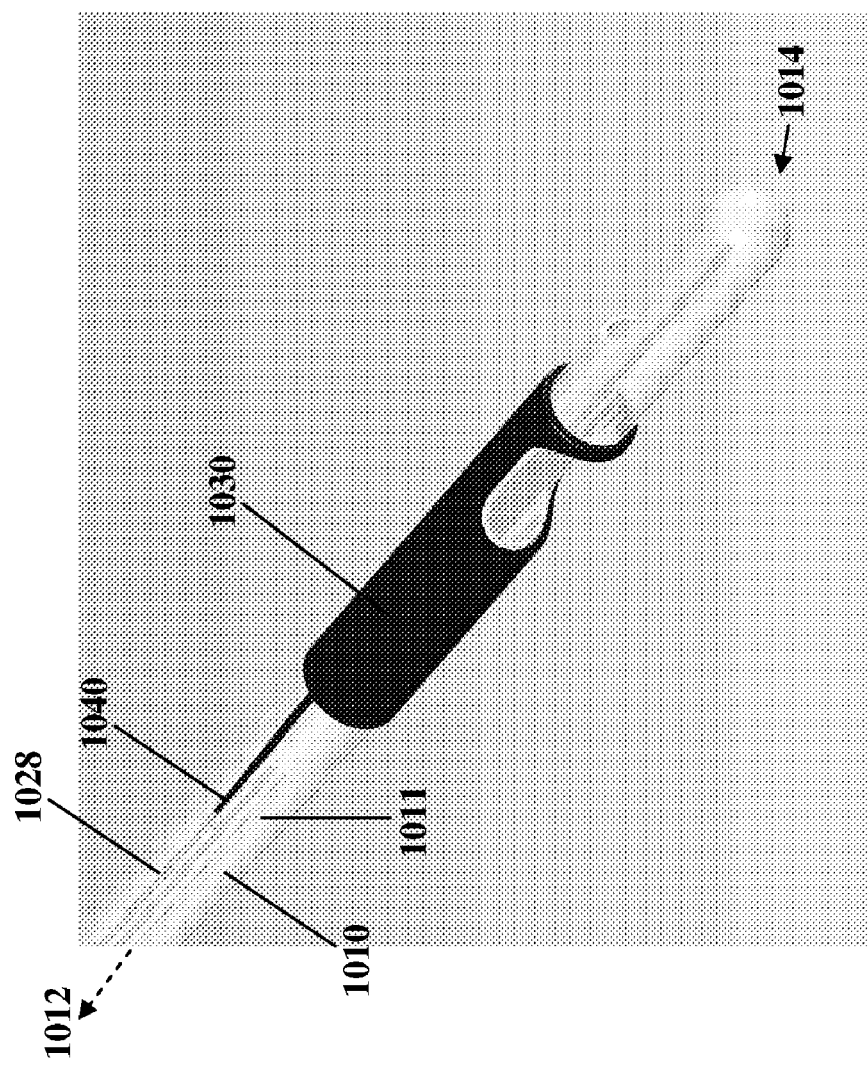
FIG. 10 illustrates an exemplary embodiment with an external control wire.

The embodiments described above employ a control wire that extends through the interior of the catheter body. However, as shown in FIG. 10, an embodiment of the present invention may employ a control wire 1040 that is positioned in a control wire channel 1028 that is not located within an interior dividing wall. The control wire channel 1028 in FIG. 10 is connected to a valve mechanism 1030 at the distal end 1014 and extends along the body wall 1011 of the catheter body 1010 to the proximal end 1012.

Figure 11A:
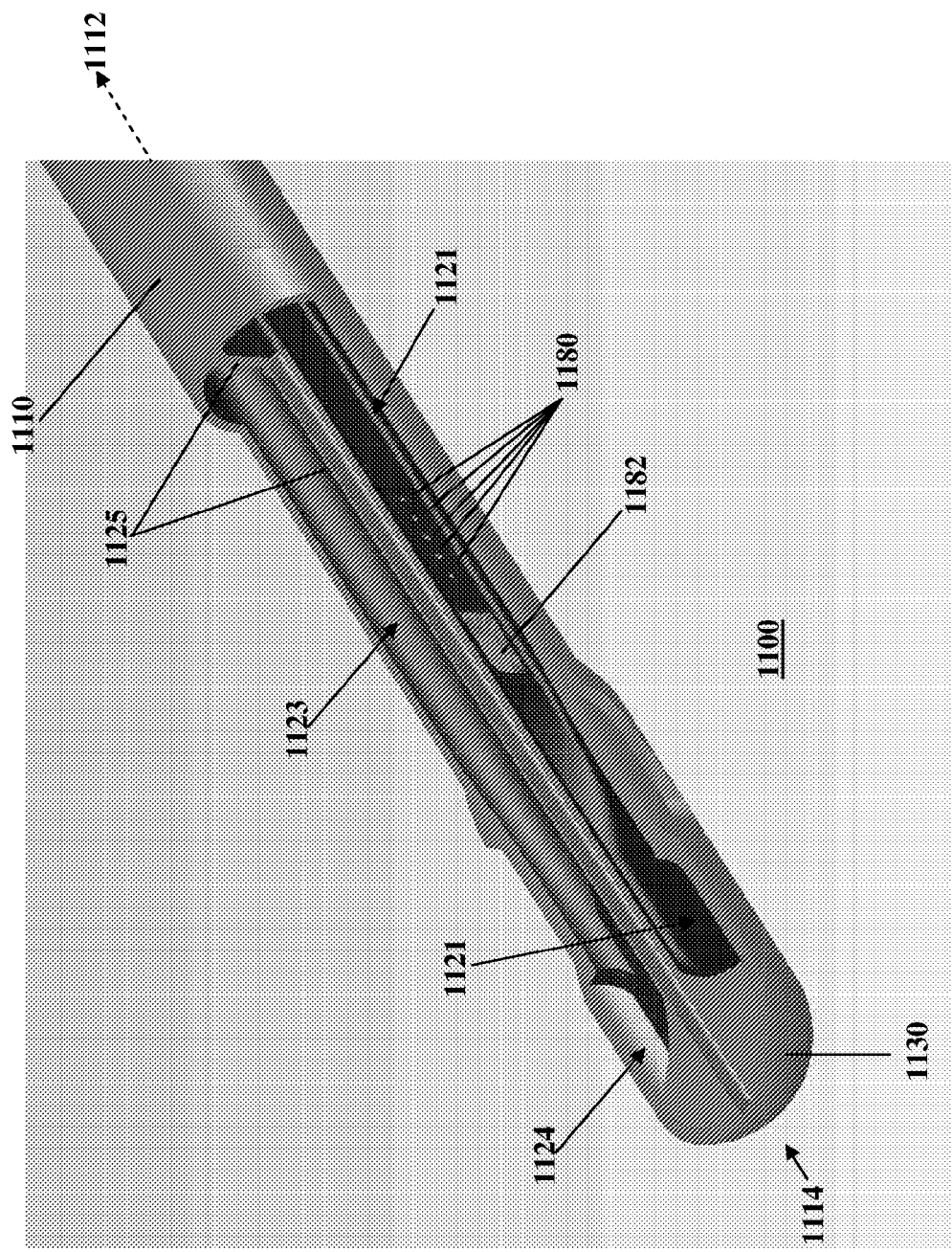
FIG. 11A illustrates an exemplary embodiment with micro-holes and a connecting valve connecting two interior chambers.

As described previously, a dangerous catheter complication is infection caused by microbial colonization on the catheter. As a result, it may be advantageous to provide a continuous flush through the interior chamber(s) of the catheter. In particular, the interior chambers may be flushed with an anti-microbial fluid. A catheter 1100 with two interior chambers 1121 and 1123 is shown in FIG. 11A. The catheter 1100 employs micro-holes 1180 that extend through the dividing wall 1125 defining the interior chambers 1121 and 1123. The micro-holes 1180, for example, may have a diameter in the range of approximately 0.015 to 0.050 inches. Although FIG. 11A illustrates the micro-holes 1180, other embodiments may employ other types of fluidic connecting channels between the two interior chambers 1121 and 1123. For instance, an embodiment may employ a slit-shaped opening defined by a longitudinal cut through the dividing wall 1125.

Furthermore, other embodiments may employ at least one connecting valve 1182 that also extends through the dividing wall 1125. The connecting valve 1182 may be selectively operated from the proximal end with an auxiliary control wire (not shown) to open a connecting valve wall (not shown) and fluidically connect the interior chambers 1121 and 1123 together.

As shown in FIG. 11A, the connecting valve 1182 may be used in combination with the micro-holes 1180. The micro-holes 1180 and the connecting valve 1182, therefore, fluidically connect the two interior chambers 1121 and 1123. When the valve mechanism 1130 moves into the closed valve position and blocks flow through the chamber openings 1122 and 1124, the introduction of a flushing fluid into the interior chambers 1121 and 1123 results in micro-distal tip communication. In other words, fluid passes through the micro-holes 1180 and/or the connecting valve 1182, causing fluid circulation through the interior chambers 1121 and 1123 without systemic spillage. As described previously, the valve mechanism in the present invention, in the closed valve position, substantially prevents or minimizes the loss of fluid from interior chambers of the catheter. Thus, when a continuous flush is introduced through catheter 1100, the valve mechanism 1130 substantially prevents the flushing fluid in the interior chambers 1121 and 1123 from entering the body passageway, or fluid from the body passageway, such as blood, from entering the interior chambers 1121 and 1123. Without the barrier created by the valve mechanism 1130, any density gradient between fluid in the passageway and fluid in the interior chambers 1121 and 1123 would cause unwanted exchange of fluid between the passageway and the interior chambers 1121 and 1123. Furthermore, the valve mechanism 1130 substantially prevents vacuum loss by the entrance of fluid from the passageway and permits a sufficient vacuum to be created within the interior chambers to initiate flushing through the interior chambers 1121 and 1123.

In addition to permitting aggressive catheter flushing, the micro-holes 1180 or the connecting valve 1182 facilitate the removal of fluid from the catheter 1100 when the chamber openings 1122 and 1124 are closed by the valve mechanism 1130. The fluidic communication between the interior chambers 1121 and 1123 enabled by the micro-holes 1180 and/or the connecting valve 1182 helps to prevent a vacuum from forming within any one of the interior chambers 1121 and 1123 when the fluid is withdrawn from the chamber, for example, with a syringe at the proximal end 1112 of the catheter. Fluid or air in one chamber is drawn through the micro-holes 1180 and/or the connecting valve 1182 into the second chamber to help prevent a vacuum from forming in the second chamber. A formation of a vacuum within the interior chamber would otherwise resist the withdrawal of fluid from the interior chamber.

An embodiment of a connecting valve is illustrated with the catheter 400' in FIGS. 4D-F. The catheter 400' has a connecting valve 482' that fluidically connects the interior chambers 421' and 423' with a closable interior valve opening 483' in the dividing wall 425'. The valve opening 483' is opened and closed by operation of the interior gate 484'. As shown in FIG. 4F, the interior gate 484' may be formed with the body 430'. The body 430' also includes the gates 430A' and 430B' which close the chamber openings 422' and 424', respectively. The interior gate 484' is generally aligned with the dividing wall 425'. As a result, the interior gate 484' divides the interior of the body 430' into two separate chambers 436' and 437' which align with the interior chambers 421' and 423'.

As further illustrated in FIG. 4D, the interior gate 484' opens the interior valve opening 483' when the gates 430A' and 430B' are in the closed valve position. In this way, the interior valve opening 483' interconnects the interior chambers 421' and 422' while the chamber openings 422' and 424' are covered, thus allowing the interior chambers 421' and 422' to be flushed in the manner described previously. On the other hand, as illustrated in FIG. 4E, the interior gate 484' closes the interior valve opening 483' when the gates 430A' and 430B' are in the open valve position. With the interior valve opening 483' closed, the interior chambers 421' and 423' are not interconnected and each can be used for a different function, e.g. drawing blood or delivering blood during hemodialysis.

A control wire (not shown) is positioned in a control wire chamber 426' extending along the dividing wall 425'. The control wire is connected to the interior gate 484' and is operated from the proximal end to exert a longitudinal force on the body 430' in both axial directions. Because the interior gate 484' is formed with the body 430', movement of the interior gate 484' is coupled to, and coordinated with, the movement of gates 430A' and 430B'.

When the body 430' as shown in FIG. 4D is moved longitudinally toward the proximal end 412', the interior gate 484' and gates 430A' and 430B' all move together toward the proximal end 412' until they reach the positions shown in FIG. 4E. In FIG. 4D, the interior valve opening 483' is closer to the proximal end 412' than the interior gate 484', while the gates 430A' and 430B' are aligned over the chamber openings 422' and 424'. Therefore, when the body 430' moves toward the proximal end 412', the gates 430A' and 430B' become misaligned with the chamber openings 422' and 424', and at the same time, the interior gate 484' moves or slides longitudinally into alignment to cover the interior valve opening 483'.

In contrast, when the body 430' as shown in FIG. 4E is moved longitudinally toward the distal end 414', the interior gate 484' and gates 430A' and 430B' all move together toward the distal end 412' until they reach the positions shown in FIG. 4D. In FIG. 4E, the interior gate 484' is aligned with the interior valve opening 483', while the chamber openings 422' and 424' are closer to the distal end 414' than the gates 430A' and 430B'. Therefore, when the body 430' moves toward the distal end 414', the gates 430A' and 430B' move back into alignment with the chamber openings 422' and 424', and at the same time, the interior gate 484' becomes misaligned with the interior valve opening 483'.

Figure 11B:
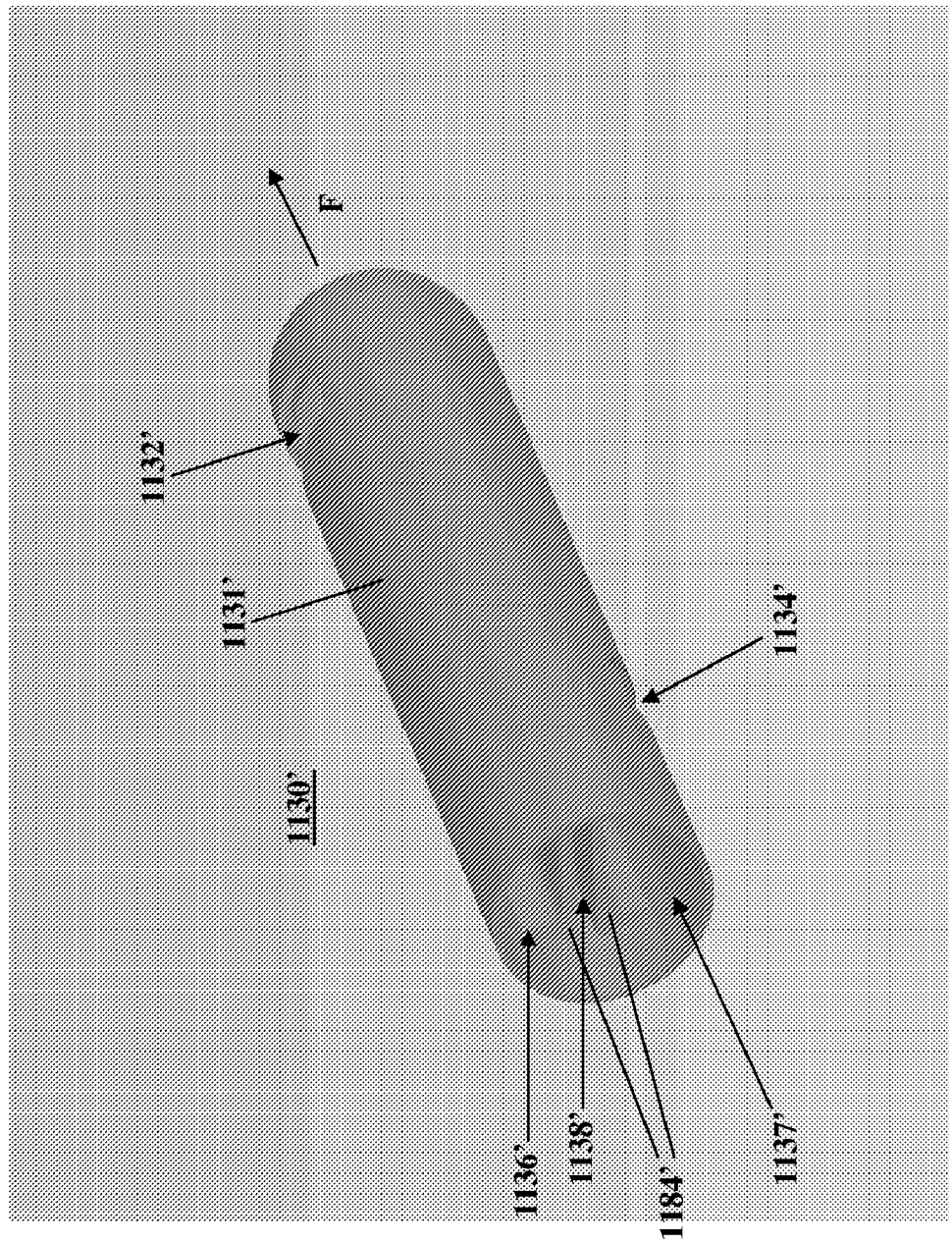
FIG. 11B illustrates an exemplary embodiment of an axially translating cap-shaped valve for use with a connecting valve connecting two interior chambers of a catheter body.

FIG. 11B illustrates a cap 1130' which is employed by an axially translating cap-shaped valve mechanism as described previously. (The cap 1130', however, is adapted to accommodate a catheter with two chamber openings that are spaced from the distal end of the catheter body by different distances.) The cap 1130' has an interior gate 1184' that controls the flow of fluid through a connecting valve that connects two interior chambers of a catheter. Like the body 430' described previously, the cap 1130' couples operation of the interior gate 1184' with the opening and closing of the chamber openings of the interior chambers in a catheter body (not shown). As the cap 1130' moves longitudinally with respect to the catheter body, the cap openings 1132' and 1134' move in and out of alignment with the chamber openings of the catheter body. When the cap openings 1132' and 1134' are aligned over the chamber openings, fluid is permitted to flow in and out of the interior chambers through the openings. With the cap openings 1132' and 1134' aligned over the chamber openings, the interior walls 1184' close the interior valve opening to substantially prevent fluidic communication between the interior chambers. When the cap 1130' is moved in the direction of arrow F shown in FIG. 11B (generally away from the proximal end of the catheter), the openings 1132' and 1134' are moved out of alignment with the chamber openings, and the wall 1131' of the cap 1130' creates barriers to the flow of fluid in and out of the interior chambers. With movement in the direction F, the interior gate 1184' opens the interior valve opening to enable fluidic communication between the interior chambers and permits the interior chambers to be flushed in the manner described above. Moving the cap 1130' opposite to the direction F blocks flow between the interior chambers again while permitting flow between the body passageway and the interior chambers.

As shown in FIG. 11B, the interior gate 1184' divides the interior of the cap 1130' into two sections 1136' and 1137' which correspond with the interior chambers of the catheter body. Moreover, a channel 1138' runs through the interior gate 1184' to allow a control wire to be extend to the tip of the cap 1130'. Operation of the control wire selectively moves the cap 1130' longitudinally.

Figures 12A, 12B, 12C:
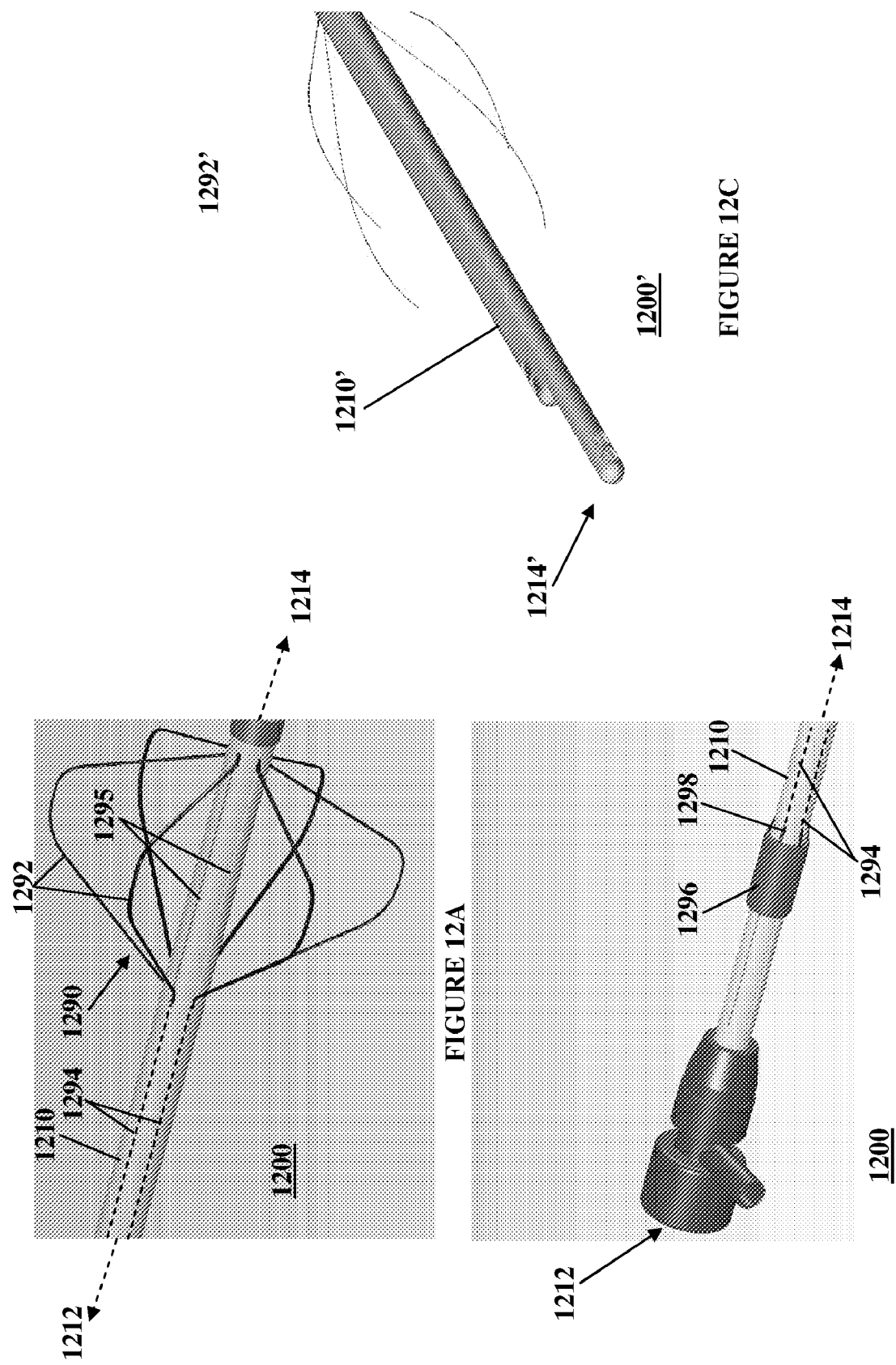
FIG. 12A illustrates a distal end of an exemplary embodiment employing elongate wires for a manually operated centering mechanism.
FIG. 12B illustrates a proximal end of the exemplary embodiment of FIG. 12A.
FIG. 12C illustrates the distal end of another exemplary embodiment employing elongate wires for a manually operated centering mechanism.

As also discussed previously, it is believed that poor catheter position or catheter kinking may also be partially responsible for the low patency rates. As such, exemplary embodiments of the present invention may employ a centering mechanism to position the catheter away from the wall of the vessel. The centering mechanism spaces the catheter from the vessel wall and substantially prevents the chamber opening of an intake chamber from being suctioned to the wall. In the embodiment of FIGS. 12A-B, the catheter 1200 employs a manually operated centering mechanism 1290 that may be expanded or contracted. Expansion of the centering mechanism 1290 occurs radially outwardly from the longitudinal line of the catheter. As shown in FIG. 12A, the centering mechanism 1290 has a plurality of elongate wires 1292, each of which has a first end secured to the catheter body 1210 adjacent to the distal end 1214. Each wire passes through an enclosed channel 1294 formed in the wall of the catheter body 1210 and extends toward the proximal end 1212 of the catheter 1200. The centering mechanism 1290 may be formed from a biocompatible material, such as NiTI, polymers, elastomers, super-alloys, and stainless steel.

As shown in FIG. 12B, near the proximal end 1212, each wire 1292 exits the respective enclosed channel 1294 and extends further to a control slide 1296 mounted for movement along the catheter body 1210. The end of each wire 1292 is secured at 1298 to the control slide 1296. When the control slide 1296 is drawn back to a position closest to the proximal end 1212, the wires 1292 at the distal end 1214 of the catheter body are drawn flat into slots 1295 in the catheter body 1210 at the distal end of each enclosed channels 1294. With the control slide 1296 at its most proximal position, each wire 1292 neatly fits into an underlying slot 1295 to maintain a smooth external catheter surface. On the other hand, movement of the control slide 1296 toward the distal end 1214 of the catheter body 1210 pushes the wires 1292 out of the slots 1295 to form the centering basket shown in FIG. 12B. The size of this centering basket is dependant upon how far the control slide 1296 is moved in the distal direction. After a dialysis session is completed, the centering basket is easily collapsed by moving the control slide back 1296 to its most proximal position. The collapsed centering basket also facilitates positioning and removal of the catheter 1200.

Although each of the plurality of elongate wires 1292 shown in FIG. 12A has a first end secured to the catheter body 1210 adjacent to the distal end 1214, the centering basket may be formed without connecting the first end to the catheter body. For instance, as shown in FIG. 12C, the wires 1292' for catheter 1200' may be formed from a flexibly resilient material that is biased to form a self-expanding centering basket when they are not drawn into, and collapsed within, the slots.

While various embodiments in accordance with the present invention have been shown and described, it is understood that the invention is not limited thereto. The present invention may be changed, modified and further applied by those skilled in the art. Therefore, this invention is not limited to the detail shown and described previously, but also includes all such changes and modifications.

What is claimed is:
1. A catheter device, the device comprising:
an elongate body with a distal end and a proximal end, the elongate body extending along a central longitudinal axis;
a chamber positioned within the elongate body, the chamber having a chamber opening;
an axially displaceable valve structure extending coaxially with the elongate body and positioned at the distal end of the elongate body, the valve structure including a barrier having a tapered section, wherein axial displacement of the valve structure causes the barrier to move relative to the chamber opening between an uncovered position where the barrier is positioned to permit flow through the chamber opening and a covered position where a proximal portion of the tapered section fits into the chamber opening such that barrier reduces flow through the chamber opening; and
a control wire connected to the valve structure and extending from the valve structure to the proximal end of the elongate body, the control wire configured to control movement of the valve structure.
2. A catheter device, the device comprising:
an elongate body, having a proximal end and a distal end, the elongate body extending along a central longitudinal axis;

a first chamber and a second chamber positioned within the elongate body, the first chamber having a first chamber opening and the second chamber having a second chamber opening;

an axially displaceable valve structure extending coaxially with the elongate body and including a first barrier and a second barrier, wherein axial displacement of the valve structure causes the first barrier to move from an uncovered position where the first barrier is positioned to permit flow through the first chamber opening to a covered position where the first barrier is positioned to reduce flow through the first chamber opening, and wherein axial displacement of the valve structure further causes the second barrier to move from an uncovered position where the second barrier is positioned to permit flow through the second chamber opening to a covered position where the second barrier is positioned to reduce flow through the second chamber opening; and a control wire operably connected to the valve structure, the control wire configured to control movement of the valve structure.

3. The device according to claim 2, further comprising an interior dividing wall positioned between the first chamber and the second chamber.

4. The device according to claim 3, further comprising at least one connecting channel positioned in the interior dividing wall and extending between the first chamber and the second chamber.

5. The device according to claim 4, wherein the at least one connecting channel comprises micro-holes.

6. The device according to claim 5, wherein the at least one connecting channel comprises a valve.

7. The device according to claim 4, further comprising a gate movable to a position closing the connecting channel.

8. The device according to claim 7, wherein the gate is operably connected to the valve structure.

9. The device according to claim 8, wherein the gate closes the connecting channel when the first barrier is moved from being positioned over the first opening and the second barrier is moved from being positioned over the second opening, and the gate opens the connecting channel when the first barrier is moved over the first opening and the second barrier is moved over the second opening.

10. The device according to claim 3, wherein the interior dividing wall includes a control wire channel, the at least one control wire positioned within the control wire channel.

11. The device according to claim 8, wherein the control wire is operably connected to the gate and the valve structure, the control wire configured to control coupled movement of the gate and the valve structure.

12. The device according to claim 11, further comprising a guide wire channel extending through the control wire from the proximal end to the distal end, the guide wire channel being adapted to accommodate a guide wire for positioning the catheter in a body passageway.

13. The device according to claim 4, further comprising:

a hub positioned at the proximal end, the hub having a first port connected to the first chamber, a second port connected to the second chamber, and a control mechanism connected to the control wire; and a seal between the control wire and the hub.

14. The device according to claim 13, wherein the seal is formed by a rolling membrane.

15. The device according to claim 4, wherein the valve structure includes a cap at the distal end of the elongate body, the first barrier and the second barrier being positioned on the cap.

16. The device according to claim 15, wherein the cap has a first cap opening configured to align with the first chamber opening and a second cap opening configured to align with the second chamber opening.

17. A hemodialysis catheter system, comprising:

an elongate body, having a proximal end and a distal end, the elongate body extending along a central longitudinal axis;

a first chamber and a second chamber positioned within the elongate body, the first chamber having a first chamber opening and the second chamber having a second chamber opening;

an axially displaceable valve structure extending coaxially with the elongate body and including a first barrier and a second barrier, wherein axial displacement of the valve structure causes the first barrier to move from an uncovered position where the first barrier is positioned to permit flow through the first chamber opening to a covered position where the first barrier is positioned to reduce flow through the first chamber opening, and wherein axial displacement of the valve structure further causes the second barrier to move from an uncovered position where the second barrier is positioned to permit flow through the second chamber opening to a covered position where the second barrier is positioned to reduce flow through the second chamber opening; and a hub secured to the proximal end, the hub including a first port and a second port, the first port coupled to the first chamber and configured to be connected to a fluid source providing a first flow into the first chamber opening, and the second port coupled to the second chamber and configured to be connected to a vacuum source providing a second flow out of the second chamber opening.

18. The device according to claim 17, wherein the first chamber opening and the second chamber opening are positioned on the elongate body according to a configuration that minimizes interference between flow through the first chamber and flow through the second chamber.

19. The device according to claim 4, wherein the valve structure includes a valve plug.

20. The device according to claim 19, wherein the first bather of the valve plug is a first tapered structure that moves to cover or uncover the first chamber opening, and the second bather of the valve plug is a second tapered structure that moves to cover or uncover the second chamber opening.

21. The device according to claim 4, wherein the first chamber opening and the second chamber opening are positioned at different longitudinal distances along the elongate body.

22. The device according to claim 21, wherein the first chamber opening is positioned closer to the distal end of the elongate body than the second chamber opening, and wherein the first bather has a first length and the second bather has a second length, the second length greater than the first length.

23. The device according to claim 1, wherein the distal end of the valve structure includes a rounded section.

24. The device according to claim 23, wherein the round section forms a bullet shaped nose.

25. The device accordingly to claim 1, wherein the catheter further comprises a second chamber having a second opening.

26. The device according to claim 25, wherein the valve structure is configured such that axial displacement of the valve structure causes the second barrier to move relative to the second chamber opening between an uncovered position where the second barrier is positioned to permit flow through the second chamber opening and a covered position where a proximal portion of the second tapered section fits into the second chamber opening such that the second barrier reduces flow through the second chamber opening.

27. The device according to claim 4, wherein the wherein the distal end of the valve structure includes a rounded section.

28. The device according to claim 27, wherein the round section forms a bullet shaped nose.

29. The device according to claim 1, wherein axial displacement comprises displacement along the central longitudinal axis of the elongate body.

30. The device according to claim 4, wherein axial displacement comprises displacement along the central longitudinal axis of the elongate body.

31. The device according to claim 17, wherein axial displacement comprises displacement along the central longitudinal axis of the elongate body.

* * * * *